US010468137B1

United States Patent
McNair et al.

(10) Patent No.: US 10,468,137 B1
(45) Date of Patent: Nov. 5, 2019

(54) MANAGING TREATMENT OF CHILDREN WITH TETRALOGY OF FALLOT

(71) Applicant: Cerner Innovation, Inc., Kansas City, KS (US)

(72) Inventors: Douglas S. McNair, Leawood, KS (US); Sasanka Are, Kansas City, MO (US); Kanakasabha Kailasam, Olathe, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 573 days.

(21) Appl. No.: 14/304,165

(22) Filed: Jun. 13, 2014

Related U.S. Application Data

(60) Provisional application No. 61/835,448, filed on Jun. 14, 2013.

(51) Int. Cl.
*G16H 50/30* (2018.01)

(52) U.S. Cl.
CPC ................... *G16H 50/30* (2018.01)

(58) Field of Classification Search
CPC .................. G06F 19/3431; G16H 50/20–30
See application file for complete search history.

(56) References Cited

U.S. PATENT DOCUMENTS

| | | | | |
|---|---|---|---|---|
| 7,593,952 B2* | 9/2009 | Soll | ...................... | G06F 19/322 |
| 2005/0177393 A1* | 8/2005 | Sacco | .................. | G06F 19/327 |
| | | | | 705/2 |
| 2008/0009684 A1* | 1/2008 | Corsetti | ................... | A61B 5/00 |
| | | | | 600/300 |
| 2008/0059243 A1* | 3/2008 | Brackett | ............. | G06F 19/3406 |
| | | | | 705/3 |
| 2012/0253207 A1* | 10/2012 | Sarkar | ................. | G06F 19/3431 |
| | | | | 600/483 |

* cited by examiner

*Primary Examiner* — Sheetal R Paulson
(74) *Attorney, Agent, or Firm* — Shook, Hardy & Bacon, LLP

(57) ABSTRACT

Systems and methods are provided for managing treatment of children with a congenital cyanotic heart condition such as Tetralogy of Fallot (ToF) including determining predicted survival probabilities within a timeframe wherein patients await medical treatment such as surgical correction, based on amounts of a biomarker, such as BNP (brain natriuretic peptide) in serial samples of blood plasma from the subject and determining a Tetralogy of Fallot Index (TOFI®) score from the biomarker values. Some embodiments use TOFI score to determine severity and include scheduling and prioritizing medical treatment for patients based on the severity. In some embodiments, the TOFI score is calculated from a plurality of biomarker measurements, which are log-transformed and z-score transformed, by a mathematical survival predictive model, such as a Cox Proportional Hazards model. In some embodiments, the method is implemented on a mobile device, such as a smart-phone or tablet application, or via web-based or cloud-based computing services.

20 Claims, 18 Drawing Sheets

Relative rate of change of Brain Natriuretic Peptide (BNP) levels in Tetralogy of Fallot patients

| MEAN | 1.013 | ToFI | | | | | | Bertranou-Blackstone-Kirklin (BBK) |
|---|---|---|---|---|---|---|---|---|
| | | 0.10 | 0.20 | 0.50 | 1.00 | 2.00 | 5.00 | |
| t (days) | S0(t) | p(s(t)) | | | | | | BBK S0(t) |
| 1 | 0.995 | 0.998 | 0.998 | 0.997 | 0.995 | 0.987 | 0.763 | N/A |
| 7 | 0.992 | 0.997 | 0.996 | 0.995 | 0.992 | 0.979 | 0.649 | N/A |
| 30 | 0.952 | 0.980 | 0.978 | 0.971 | 0.953 | 0.876 | 0.071 | 0.95 |
| 90 | 0.886 | 0.953 | 0.948 | 0.930 | 0.887 | 0.723 | 0.001 | N/A |
| 180 | 0.791 | 0.910 | 0.901 | 0.869 | 0.793 | 0.533 | 0.000 | N/A |
| 365 | 0.663 | 0.848 | 0.833 | 0.782 | 0.667 | 0.332 | 0.000 | 0.66 |
| 730 | 0.570 | 0.798 | 0.779 | 0.714 | 0.574 | 0.221 | 0.000 | 0.57 |

1.013 is the population-mean TOFI score in HF cohort Cox Proportional Hazards model PROBABILITY FOR SURVIVAL OVER A TIME INTERVAL $S(t) = S0(t) \wedge (EXP((TOFI) - 1.013))$
(E.g., $0.998 = 0.995\wedge(e\wedge(0.10-1.013))$)

TETRALOGY OF FALLOT INDEX RECEIVER OPERATING CHARACTERISTIC (ROC) CURVE

| TOFL | SURV2SURG | DIED_A_SURG | TOTAL |
|---|---|---|---|
| 0.00-0.09 | 23 | 0 | 23 |
| 0.10-0.19 | 2 | 0 | 2 |
| 0.20-0.49 | 1 | 0 | 1 |
| 0.50-0.99 | 0 | 3 | 3 |
| 1.0-1.9 | 1 | 5 | 6 |
| 2.0-4.9 | 2 | 11 | 13 |
| 5.0+ | 0 | 3 | 3 |
|  | 29 | 22 | 51 |

| | 905 | 910 | 920 | 925 | 930 | 935 | 940 | 945 | 950 | 960 | 970 | 980 |
|---|---|---|---|---|---|---|---|---|---|---|---|---|
| PAT | BNP | BNPV | VNORM | SDS1 | SDS2' | SDS2 | RL | time | status | x | TOFI | TGT1 |
| 1 | 79.9 | 1.28 | 0.016 | 0.144 | 0.000 | 0.000 | 1 | 441 | 0 | 1 | 0.309 | 0 |
| 2 | 29.8 | 0.62 | 0.021 | 0.000 | 0.000 | 0.000 | 0 | 331 | 0 | 1 | 0.000 | 0 |
| 3 | 132.2 | 4.73 | 0.036 | 1.043 | 1.613 | 0.000 | 1 | 22 | 0 | 1 | 2.233 | 1 |
| 4 | 22.8 | 0.97 | 0.043 | 0.000 | 0.000 | 0.000 | 0 | 457 | 0 | 1 | 0.000 | 0 |
| 5 | 23.2 | 1.11 | 0.048 | 0.000 | 0.000 | 0.000 | 0 | 348 | 0 | 1 | 0.000 | 0 |
| 6 | 29.8 | 1.59 | 0.053 | 0.000 | 0.268 | 0.000 | 1 | 207 | 0 | 1 | 0.000 | 0 |
| 7 | 18.8 | 0.96 | 0.051 | 0.000 | 0.000 | 0.000 | 0 | 474 | 0 | 1 | 0.000 | 0 |
| 8 | 56.9 | 1.86 | 0.033 | 0.000 | 0.461 | 0.000 | 0 | 96 | 0 | 1 | 0.000 | 0 |
| 9 | 16.6 | 0.69 | 0.042 | 0.000 | 0.000 | 0.000 | 0 | 610 | 0 | 1 | 0.000 | 0 |
| 10 | 23.25 | 1.55 | 0.067 | 0.000 | 0.236 | 0.151 | 0 | 274 | 0 | 1 | 0.170 | 0 |
| 11 | 25.4 | 1.37 | 0.054 | 0.000 | 0.084 | 0.000 | 0 | 288 | 0 | 1 | 0.000 | 0 |
| 12 | 9.4 | 0.47 | 0.050 | 0.000 | 0.000 | 0.000 | 0 | 658 | 0 | 1 | 0.000 | 0 |
| 13 | 6.8 | 0.46 | 0.068 | 0.000 | 0.000 | 0.175 | 0 | 661 | 0 | 1 | 0.196 | 0 |
| 14 | 12.2 | 0.56 | 0.046 | 0.000 | 0.000 | 0.000 | 0 | 570 | 0 | 1 | 0.000 | 0 |
| 15 | 128.3 | 2.79 | 0.022 | 0.990 | 0.962 | 0.000 | 1 | 25 | 0 | 1 | 2.118 | 1 |
| 16 | 47.2 | 2.04 | 0.043 | 0.000 | 0.575 | 0.000 | 1 | 71 | 0 | 1 | 0.000 | 0 |
| 17 | 16.4 | 0.67 | 0.041 | 0.000 | 0.000 | 0.000 | 0 | 505 | 0 | 1 | 0.000 | 0 |
| 18 | 97.6 | 1.53 | 0.016 | 0.502 | 0.220 | 0.000 | 1 | 130 | 0 | 1 | 1.073 | 1 |
| 19 | 14.9 | 0.61 | 0.041 | 0.000 | 0.000 | 0.000 | 0 | 489 | 0 | 1 | 0.000 | 0 |
| 20 | 56.7 | 2.22 | 0.039 | 0.000 | 0.680 | 0.000 | 1 | 52 | 0 | 1 | 0.000 | 0 |
| 21 | 18.1 | 0.91 | 0.050 | 0.000 | 0.000 | 0.000 | 0 | 478 | 0 | 1 | 0.000 | 0 |
| 22 | 46.1 | 2.17 | 0.047 | 0.000 | 0.652 | 0.000 | 0 | 71 | 0 | 1 | 0.000 | 0 |
| 23 | 24.6 | 1.25 | 0.051 | 0.000 | 0.000 | 0.000 | 0 | 258 | 0 | 1 | 0.000 | 0 |
| 24 | 10.1 | 0.47 | 0.047 | 0.000 | 0.000 | 0.000 | 0 | 653 | 0 | 1 | 0.000 | 0 |
| 25 | 13.7 | 0.79 | 0.058 | 0.000 | 0.000 | 0.000 | 0 | 512 | 0 | 1 | 0.000 | 0 |
| 26 | 44.2 | 2.18 | 0.049 | 0.000 | 0.657 | 0.000 | 0 | 97 | 0 | 1 | 0.000 | 0 |
| 27 | 30.9 | 1.74 | 0.056 | 0.000 | 0.379 | 0.000 | 0 | 139 | 0 | 1 | 0.000 | 0 |
| 28 | 16.7 | 0.85 | 0.051 | 0.000 | 0.000 | 0.000 | 0 | 651 | 0 | 1 | 0.000 | 0 |
| 29 | 29.9 | 1.42 | 0.047 | 0.000 | 0.128 | 0.000 | 0 | 190 | 0 | 1 | 0.000 | 0 |
| 30 | 78.4 | 7.4 | 0.094 | 0.110 | 2.166 | 0.681 | 1 | 461 | 1 | 1 | 0.998 | 0 |
| 31 | 213.2 | 15.9 | 0.075 | 1.897 | 3.110 | 0.328 | 1 | 187 | 1 | 1 | 4.426 | 1 |
| 32 | 298.3 | 15.7 | 0.053 | 2.497 | 3.095 | 0.000 | 1 | 128 | 1 | 1 | 5.343 | 1 |
| 33 | 74.2 | 6.9 | 0.093 | 0.012 | 2.080 | 0.664 | 1 | 470 | 1 | 1 | 0.769 | 0 |
| 34 | 314.8 | 16.3 | 0.052 | 2.593 | 3.141 | 0.000 | 1 | 116 | 1 | 1 | 5.548 | 1 |
| 35 | 56.9 | 6.7 | 0.118 | 0.000 | 2.043 | 1.036 | 0 | 478 | 1 | 1 | 1.160 | 1 |

900

CONTINUES IN FIG. 9C

*FIG. 9B*

CONTINUES FROM FIG. 9B
.
.
.

| PAT | BNP | BNPV | VNORM | SDS1 | SDS2' | SDS2 | RL | time | status | x | TOFI | TGT1 |
|---|---|---|---|---|---|---|---|---|---|---|---|---|
| 36 | 113.3 | 10.1 | 0.089 | 0.768 | 2.550 | 0.595 | 1 | 552 | 1 | 1 | 2.310 | 1 |
| 37 | 171.9 | 17.5 | 0.102 | 1.512 | 3.229 | 0.808 | 1 | 156 | 1 | 1 | 4.142 | 1 |
| 38 | 110.6 | 10.9 | 0.099 | 0.725 | 2.644 | 0.762 | 1 | 273 | 1 | 1 | 2.404 | 1 |
| 39 | 76.5 | 7.6 | 0.099 | 0.067 | 2.199 | 0.762 | 1 | 442 | 1 | 1 | 0.995 | 0 |
| 40 | 16.1 | 4.1 | 0.255 | 0.000 | 1.437 | 2.240 | 0 | 12 | 1 | 1 | 2.509 | 1 |
| 41 | 20.7 | 5.2 | 0.251 | 0.000 | 1.730 | 2.215 | 1 | 651 | 1 | 1 | 2.481 | 1 |
| 42 | 34.4 | 4.8 | 0.140 | 0.000 | 1.632 | 1.303 | 0 | 729 | 1 | 1 | 1.459 | 1 |
| 43 | 157.8 | 11.3 | 0.072 | 1.360 | 2.689 | 0.264 | 1 | 50 | 1 | 1 | 3.205 | 1 |
| 44 | 189.7 | 13.2 | 0.070 | 1.688 | 2.881 | 0.220 | 1 | 170 | 1 | 1 | 3.859 | 1 |
| 45 | 98.9 | 14.1 | 0.143 | 0.525 | 2.962 | 1.336 | 1 | 442 | 1 | 1 | 2.620 | 1 |
| 46 | 110.9 | 13.8 | 0.124 | 0.730 | 2.935 | 1.113 | 1 | 223 | 1 | 1 | 2.808 | 1 |
| 47 | 88.6 | 8.1 | 0.091 | 0.329 | 2.278 | 0.630 | 1 | 415 | 1 | 1 | 1.409 | 1 |
| 48 | 92.51 | 10.2 | 0.110 | 0.406 | 2.562 | 0.926 | 1 | 578 | 1 | 1 | 1.906 | 1 |
| 49 | 102.4 | 9.4 | 0.092 | 0.587 | 2.461 | 0.647 | 1 | 296 | 1 | 1 | 1.981 | 1 |
| 50 | 349.6 | 21.1 | 0.060 | 2.780 | 3.460 | 0.000 | 1 | 176 | 1 | 1 | 5.949 | 1 |
| 51 | 106.8 | 9.4 | 0.088 | 0.662 | 2.461 | 0.577 | 1 | 274 | 1 | 1 | 2.064 | 1 |

900

901

| | |
|---|---|
| 10th | 0.000 |
| 25th | 0.000 |
| median | 0.000 |
| 75th | 2.272 |
| 90th | 3.859 |
| | |
| mean TOFI | 1.303 |
| StdDev TOFI | 1.667 |

*FIG. 9C*

```
library(survival)
# ToFI Cox Proportional Hazards models
# tofi1 <- coxph(Surv(time, status) ~ x + SDS1 + SDS2 + strata(RL), data=tofi)
# tofi2 <- coxph(Surv(time, status) ~ x + SDS1 + SDS2 + RL + tt(time),
#     tt=function(x,t,...) pspline(x + t/365.25), data=tofi)
#     tofi3 <- coxph(Surv(time, status) ~ SDS1 + SDS3, data=tofi)
# Note that RL as predictor var [instead of strata var] gives p > 0.3 n.s.

# n= 51, number of events= 22

#       coef  exp(coef) se(coef)    z    Pr(>|z|)
# SDS1 2.1392   8.4924   0.4084  5.238  1.62e-07 ***
# SDS3 1.1177   3.0578   0.3663  3.052  2.28e-03 **
# ---
# Signif. codes:  0 '***' 0.001 '**' 0.01 '*' 0.05 '.' 0.1 ' ' 1

#       exp(coef) exp(-coef) lower .95 upper .95
# SDS1    8.492     0.1178    3.814    18.909
# SDS3    3.058     0.3270    1.492     6.269

# Concordance= 0.90  (se = 0.068)
# Rsquare= 0.545   (max possible= 0.927)
# Likelihood ratio test = 40.2  on 2 df,  p=1.9e-09
# Wald test            = 29.2  on 2 df,  p=4.6e-07
# Score (logrank) test = 62.4  on 2 df,  p=2.8e-14
```

| Patient Data | enter | |
|---|---:|---|
| # BNP values to regress (enter 2 to 5) | 4 | :-):-):-) |
| Date of the first BNP | 1-Feb-13 | :-):-):-) |
| BNP #1 | 80 | pg/mL |
| Date of the second BNP | 30-Apr-13 | :-):-):-) |
| BNP #2 | 128 | pg/mL |
| Date of the third BNP | 22-May-13 | :-):-):-) |
| BNP #3 | 124 | pg/mL |
| Date of the fourth BNP | 1-Jun-13 | :-):-):-) |
| BNP #4 | 162 | pg/mL |
| Date of the fifth BNP | | :-):-):-) |
| BNP #5 | | pg/mL |

1050

| calculate | result | | |
|---|---:|---|---|
| Data complete? | Yes | | |
| Time between 1st and 2nd specimen | 2.89 | yr | |
| BNP velocity between 1st and 2nd specimen | 16.6 | pg/mL/mo | increased |
| Time between 2nd and 3rd specimen | 0.72 | yr | |
| BNP velocity between 2nd and 3rd specimen | -5.5 | pg/mL/mo | :-):-):-) |
| Time between 3rd and 4th specimen | 0.33 | yr | |
| BNP velocity between 3rd and 4th specimen | 115.7 | pg/mL/mo | increased |
| (Only 4 specimines provided) | -- | yr | |
| (Only 4 specimines provided) | -- | pg/mL/mo | |
| Velocity (linear regression of all BNP values) | 43.7 | pg/mL/mo | |
| Slope (regression of ln(BNP) vs ln(mo)) | 0.1291 | | |
| Slope (regression of ln(BNP) vs days) | 0.0051 | | |
| BNP doubling time | 135 | | |
| Each doubling of time gives this % increase in BNP | 38.2% | | |

*FIG. 10A.*

| days | BNP | mo | ln(BNP) | ln(mo) |
|---|---|---|---|---|
| 0 | 80 | 0 | 4.382 | -0.500 |
| 88 | 128 | 34.69 | 4.852 | 3.547 |
| 110 | 124 | 43.37 | 4.820 | 3.770 |
| 120 | 162 | 47.31 | 5.088 | 3.857 |
| - | - | - | - | - |

MANAGING TREATMENT OF CHILDREN WITH TETRALOGY OF FALLOT

CROSS-REFERENCE TO RELATED APPLICATIONS

This application claims the benefit of U.S. Provisional Application No. 61/835,448, titled "MANAGING TREATMENT OF CHILDREN WITH TETRALOGY OF FALLOT," filed Jun. 14, 2013, which is hereby expressly incorporated by reference in its entirety.

INTRODUCTION

Tetralogy of Fallot (ToF) is one of the most common congenital heart disorders. Most infants with ToF require some type of surgical corrective procedure. Surgery is preferably done at or about 12 months of age. However, the timing of the surgery depends on the severity of the ToF. The mortality rate in untreated patients exceeds 50% by age 6 years, but in the present era of cardiac surgery, children with simple forms of ToF can enjoy good long-term survival with an excellent quality of life.

Mature human Brain Natriuretic Peptide (B-type Natriuretic Peptide; BNP) is produced by cardiac myocytes of the ventricles of the heart in response to abnormal ventricular wall stress and loading conditions. BNP is involved in the natriuresis system to regulate fluid balance and blood pressure. Increased levels of BNP in the blood, serum or plasma of a patient can indicate left-ventricular dysfunction. Therefore BNP can be used as a biomarker in assessing the perioperative status of ToF patients. Further, determining a rate of change of BNP over time may be used for more accurately forecasting survival and mortality risk of patients with ToF.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Embodiments of the present invention relate generally to accurately forecasting survival or mortality risk for patients with ToF. In this regard, prognoses can be determined based on determined levels of BNP in serial samples of blood plasma and computing a TOFI score for a predictive model, based on BNP levels. Embodiments of the invention can facilitate assessing the perioperative status of ToF patients. Embodiments can also facilitate decision making regarding provisioning health care resources.

BRIEF DESCRIPTION OF THE DRAWINGS

Embodiments are described in detail below with reference to the attached drawing figures, wherein:

FIGS. 9B and 9C provide a table of example patient data from a cohort of ToF patients and calculations based on the data, in accordance with embodiments of the present invention;

FIG. 9D shows an example algorithm for determining a TOFI score using a Cox proportional hazards model; and FIGS. 10A and 10B illustratively depict example graphical user interface components for receiving patient information and displaying results to a clinician or caregiver, suitable to implement embodiments of the present invention.

DETAILED DESCRIPTION

Figure 1A:
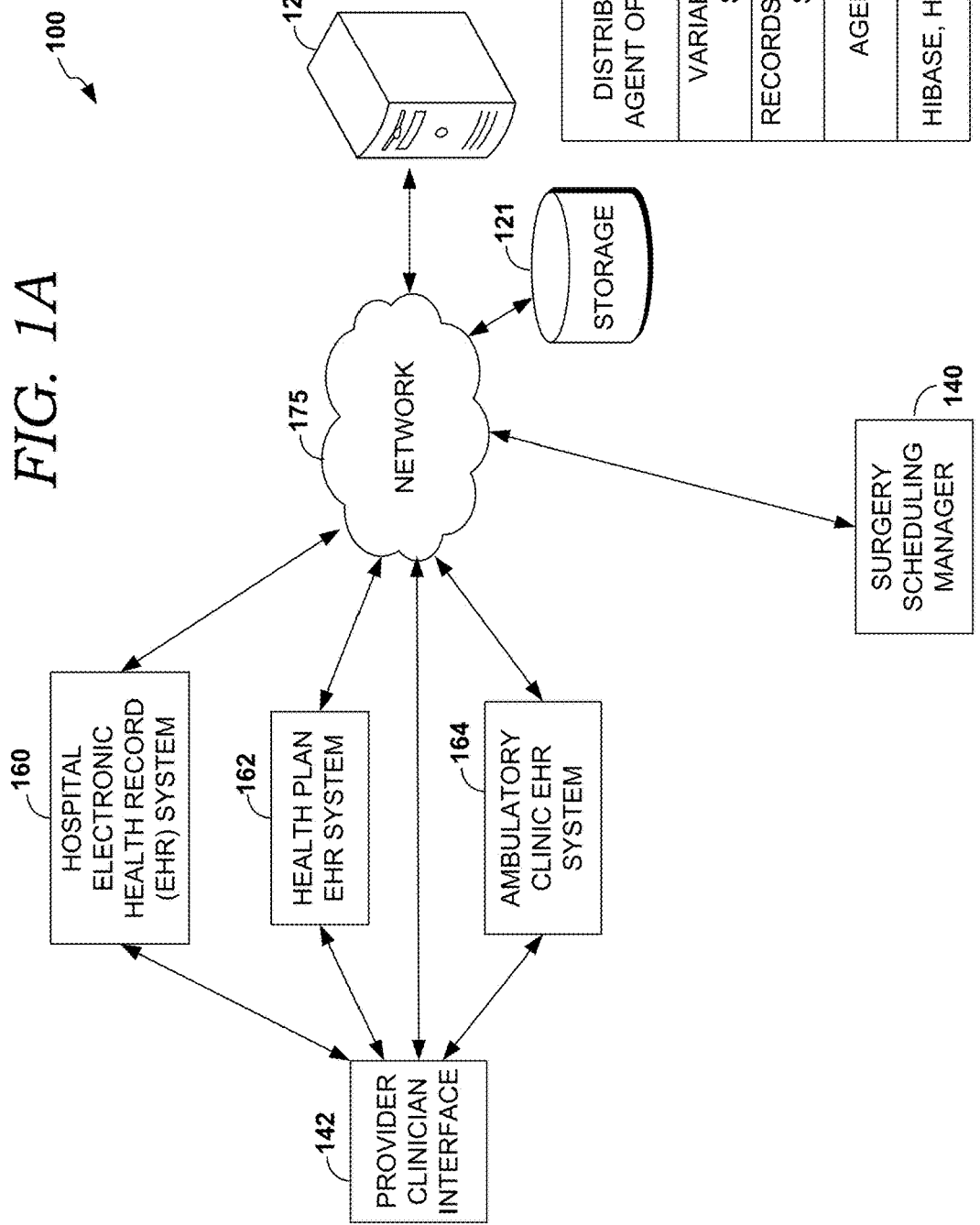
FIGS. 1A and 1B depict aspects of an exemplary operating environment suitable to implement embodiments of the present invention.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media.

Computer-readable media include both volatile and nonvolatile media, removable nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other storage devices. These technologies can store data momentarily, temporarily, or permanently.

Embodiments of the present invention are directed to systems, methods, and computer-readable media for facilitating the use of biomarkers in determining severity of ToF and for determining a predictive model for determining prognoses, such as in terms of a predicted survival probability, within a timeframe for a subject whose congenital cyanotic heart condition known as ToF awaits surgical correction. The velocity of the biomarkers Brain Natriuretic Peptide (BNP), N-terminal Brain Natriuretic Peptide (NT-BNP), or pro-NT-BNP can be used for determining the severity of ToF. For example, in some embodiments, based on determining the amount of BNP (brain natriuretic peptide) in serial samples of blood plasma from said subject, a Tetralogy of Fallot Index (TOFI™) score is determined based on the BNP values. Some embodiments further comprise determining an amount of right-to-left shunt flow ascertained by cardiac imaging studies of said subject, and applying this measurement in the predictive mathematical model. Some embodiments also further comprise utilizing the TOFI score(s) as an aid to clinically appropriate, fair, and equitable scheduling of subjects for corrective surgery in settings where the resources to perform pediatric cardiac surgery are in short supply or for automatically determining and recommending such a schedule. Further, in some embodiments, a TOFI score is calculated from a plurality of BNP measurements, log-transformed and z-score transformed, by a mathematical survival predictive model, such as a Cox Proportional Hazards model, which may be carried out on a local or mobile device, such as a smart-phone or tablet application, or via a web-based or cloud-based computing services.

ToF is a combination of four heart defects that causes a change in the normal flow of blood through the heart. The four heart defects include (1) right ventricular (RV) outflow tract obstruction (RVOTO infundibular stenosis), (2) ventricular septal defect (VSD), (3) aorta dextroposition (overriding), and (4) RV hypertrophy. The ventricular septal defect, which is a hole in the wall of the heart between the two lower heart chambers (ventricles), causes oxygen-rich blood to mix with oxygen-poor blood.

The clinical features of ToF are directly related to the severity of the anatomic defects. Infants often display episodes of cyanosis during crying or feeding ("Tet" spells); exertional dyspnea (usually worsening with age); cyanosis of the skin, lips and nail bed; clubbing of fingers and toes; systolic thrill along the left sternal border; harsh systolic ejection murmur (SEM); RV predominance; aortic ejection click; hemoptysis; and failure to thrive. Patients with significant cyanosis can have the following, in association with a tendency to bleeding and thromboembolism: polycythemia (increased red blood cell count; increased hemoglobin and hematocrit, elevated in proportion to the degree of cyanosis), decreased clotting factors, low platelet count, diminished coagulation factors, diminished total fibrinogen, and prolonged prothrombin and coagulation times.

Most infants with ToF require some type of surgical corrective procedure. Surgery is preferably done at or about 12 months of age. However, the timing of the surgery depends on the severity of the ToF. Primary correction is the ideal operation and is usually performed under cardiopulmonary bypass. Palliative procedures (e.g., placement of the modified Blalock-Taussig shunt) may be necessary in patients with contraindications to primary repair, which include the following: presence of an anomalous coronary artery, very low birth weight, small pulmonary arteries, multiple VSDs, and multiple coexisting intracardiac malformations. The mortality rate in untreated patients exceeds 50% by age 6 years, but in the present era of cardiac surgery, children with simple forms of ToF can enjoy good long-term survival with an excellent quality of life.

However, if the damage to the heart is too severe and becomes life-threatening, urgent surgical correction is necessary. Although survival rate from pediatric open-heart surgery has steadily improved within the last four decades, repair in early infancy still puts the patient at increased risk, not only of perioperative mortality but also of the need for a greater number of subsequent re-operations. Therefore, only patients with emerging deterioration of cardiac function are taken to surgery in early infancy. For those patients, the benefits of surgical correction (restoring cardiopulmonary function) will outweigh the disadvantages.

In order to make reliable decisions regarding the treatment of patients suffering from cyanotic congenital heart conditions, the severity, i.e., the degree of cardiac impairment and secondary compensatory changes need to be carefully assessed (staging/grading). Methods used for grading abnormal heart function including, for example, echocardiography, cardiac MRI, and cardiac catheterization and angiography and ventriculography. Performing these assessments is expensive, invasive, and time-consuming. Measurement of shunt flow, ventricular ejection fraction, and other hemodynamic parameters is difficult to do precisely in small pediatric subjects. Within-individual, inter-exam variability is significant, and this may lead to incorrect staging. Delay in repair puts the patient at risk of sudden cardiac death, injury secondary to syncopal spells, stroke, and other adverse outcomes—notably ones that are associated with the ventricular septal defect, such as systemic thromboembolism and sepsis.

Brain Natriuretic Peptide (B-type Natriuretic Peptide; BNP) is produced by cardiac myocytes of the ventricles of the heart in response to abnormal ventricular wall stress and loading conditions. BNP is involved in the natriuresis system to regulate fluid balance and blood pressure. Proteolytic cleavage of the biologically inactive 108 amino acid pro-NT-BNP (pro-BNP) precursor molecule results in the 32 amino acid biologically active BNP peptide and the 76 amino acid N-terminal Brain Natriuretic Peptide NT-BNP (NT-proBNP).

The signs and symptoms of acute and chronic cardiac decompensation are frequently non-specific, highly variable, and may also be observer dependent, thereby rendering accurate diagnosis a significant clinical challenge. In this connection, BNP testing is useful for the diagnostic evaluation of patients with dyspnea and suspected acute heart failure. BNP determinations also may be used to predict prognosis in individuals with non-CHF states, such as coronary artery disease, pulmonary embolism (PE), critical illness, and following cardiac transplantation. Since increased levels of BNP in the blood, serum or plasma of a patient can indicate left-ventricular dysfunction, it can be used as a biomarker in assessing the perioperative status of ToF patients.

Several limitations in ToF testing exists, including: (1) excessive false-negative error rate (false misses, and consequent failure to allocate case-management and care-coordination services optimally), associated mainly with analytical imprecision of imaging-based measurements; (2) excessive false-positive error rate (false hits), associated mainly with wide within-subject variability of the measurements; (3) failure to accurately represent the continuum of physiology and progression of illness and its complications; (4) no forecasting of the likely timing of the adverse outcome to be averted; (5) weak relationship to operative procedure needed and relevant anatomy; (6) excessive reliance on invasive or expensive imaging and other diagnostic procedures; (7) reliance on large number of input variables to produce prediction or score; and (8) some prognostic scores, such as VIS are only relevant in the post-operative interval.

The consequences of these limitations include the following: (1) under-prediction of true mortality risk, leading to deaths while on the waiting list, including some deaths that could have been prevented; (2) unfair queueing and allocation of regional capacity to perform corrective surgeries, allocating more capacity to some subjects or groups of subjects, while under-allocating capacity to others; (3) queueing delays, resulting in excess morbidity or other bad outcomes; and (4) failure to rectify access and schedule root-causes of delays. Therefore, there is a need for embodiments of the means, methods, and systems described herein for allowing an assessment of the severity of abnormalities associated with ToF and accurate prediction of mortality risk; which facilitate reliable efficient prognosis; and which can mitigate the aforementioned limitations.

Predictive models can be utilized for triaging and prioritizing patients for access to surgical and medical resources or other treatment that are in short supply, according to the risk to which the patient is exposed. For example, the MELD system (model of end-stage liver disease) is a mathematical model for assessing liver dysfunction and predicting mortality risk. MELD allows for identifying those patients who most urgently need a liver transplant and adjusting the position of individual patients in the queue or waiting list to receive a transplant, based on a determined score for each patient. The higher the MELD score, the more urgent is the need of a patient for a transplant and the higher the position of that patient in the waiting list.

However, to date there is no quantitative score or method for objectively assessing mortality risk in pediatric ToF patients, including for the purpose of managing the scheduling and transfer of patients for surgical corrective procedures. Accordingly a further aspect of some embodiments of the present invention includes providing a system for ToF staging and pediatric open-heart surgery queue management capable of performing in a manner similar to how MELD system is used for liver transplantation.

Some embodiments of the invention include determining a longitudinal, repeated calculation of Tetralogy of Fallot Index (TOFI score) from serial determinations of biomarker variables used in a predictive model, which enables discovery of changes in severity or prognosis. In this way, these embodiments can include (1) utilization of a time series of plasma BNP values, which constitute a biomarker for the severity of myocardial ventricular decompensation; (2) calculation of the rate of change (slope or velocity) in arrears of BNP with respect to time and, from this, calculate the relative rate of change with respect to the absolute BNP value at the time of the velocity measurement; (3) log-transforming BNP and relative BNP velocity to remove right-skewness from their distributions; (4) transforming the de-skewed BNP and relative BNP velocity to z-scores; and (5) applying a survival time-to-event mathematical model utilizing these z-score values (such as a Cox Proportional Hazards model), to forecast mortality likelihood according to algorithms that are already known to those practiced in the art.

In one aspect, a method for monitoring a person having ToF is provided, wherein the method includes obtaining a first biological sample from a patient at a first time; determining an amount of one or more of Brain Natriuretic Peptide (BNP), N-terminal Brain Natriuretic Peptide (NT-BNP), or pro-NT-BNP in the first biological sample; obtaining a second biological sample from the patient at a second time later than the first time; and determining an amount of one or more of Brain Natriuretic Peptide (BNP), N-terminal Brain Natriuretic Peptide (NT-BNP), or pro-NT-BNP in the second biological sample; determining a velocity of one or more of Brain Natriuretic Peptide (BNP), N-terminal Brain Natriuretic Peptide (NT-BNP), or pro-NT-BNP of at least the first and second biological samples. The method also includes comparing the velocity of the one or more of Brain Natriuretic Peptide (BNP), N-terminal Brain Natriuretic Peptide (NT-BNP), or pro-NT-BNP of at least the first and second biological samples to control velocity measurements. The method further includes determining a severity of the ToF based on the comparison of the velocities.

In another aspect, a method for monitoring patients having ToF is provided, wherein the method includes obtaining a first biological sample from a patient at a first time and determining an amount of one or more of BNP, NT-BNP, or pro-NT-BNP from the first biological sample. The method also includes obtaining a second biological sample from the same patient at a second time, which is later than the first time, and determining an amount of one or more of BNP, NT-BNP, or pro-NT-BNP from the second biological sample. The method further includes determining the velocity of BNP, NT-BNP, or pro-NT-BNP amount(s) from at least the first and second biological samples. Subsequently, the velocity is compared to control velocity measurements. Based on this comparison, a severity of the ToF is then determined.

In another aspect, a method for ranking ToF patients that require medical treatment for the ToF is provided, wherein the method includes obtaining a velocity of one or more of Brain Natriuretic Peptide (BNP), N-terminal Brain Natriuretic Peptide (NT-BNP), or pro-NT-BNP from biological samples from a first patient and a second patient followed by comparing the velocity of the one or more of Brain Natriuretic Peptide (BNP), N-terminal Brain Natriuretic Peptide (NT-BNP), or pro-NT-BNP from the first patient and the second patient. The method also includes ranking the first and second patient based on the comparison of the velocities, wherein the ranking is based on a numbering system in which the higher the number the more urgent the need for medical treatment of the ToF.

In another aspect, a method of determining if a ToF patient is eligible for urgent surgical correction is provided, wherein the method includes obtaining a velocity of one or more biomarkers of Brain Natriuretic Peptide (BNP), N-terminal Brain Natriuretic Peptide (NT-BNP), or pro-NT-BNP from a biological sample from a patient followed by comparing the velocity of the one or more of Brain Natriuretic Peptide (BNP), N-terminal Brain Natriuretic Peptide (NT- BNP), or pro-NT-BNP of the biological sample to control velocity measurements of the one or more biomarkers. The method also includes determining an amount of one or more markers of lactic acid, cardiac index, right atrial pressure, central venous pressure, right ventricular ejection fraction, rapid shallow breathing index (Tobin score), ration of VSD shunt flow to systemic flow, and right-to-left shunt flow from a biological sample from a patient; comparing the amount of each of the markers to a reference amount for each of the markers determined; and determining if the patient is eligible for urgent surgery based on results of the comparison of the biomarkers and the comparison of the markers.

In another aspect, a method is provided for determining that a ToF patient is eligible for urgent surgical correction, wherein the method includes determining an amount of one or more markers of Brain Natriuretic Peptide (BNP), N-terminal Brain Natriuretic Peptide (NT-BNP), pro-NT-BNP, lactic acid, cardiac index, right atrial pressure, central venous pressure, right ventricular ejection fraction, rapid shallow breathing index (Tobin score), ratio of VSD shunt flow to systemic flow, and right-to-left shunt flow. The method also includes comparing the amount of each of the markers to a reference amount for each of the markers. The method further includes determining that the patient is eligible for urgent surgery based on the results of the comparison.

In another aspect, a method, or computer readable media having computer-executable instructions embodied thereon for performing a method, is provided for facilitate a method of clinical decision-making, wherein the method includes receiving a first set of information associated with a patient having a pediatric cardiac condition, the information including a plurality of timed measurements of a biomarker; receiving a second set of information associated with a reference population of one or more patients having the same pediatric cardiac condition; and based on the first set of information, determining a rate of change for the biomarker measurements. The method also includes determining a severity score indicative of the pediatric cardiac condition for the patient, based on the determined rate of change and the second set of information. The method further includes determining a schedule for treating the patient based on the severity score. In some embodiments, the method further includes applying a predictive model to determine a probability of survival, based on the determined severity score. In some embodiments, the method further includes assigning a priority for treatment of the patient based on the determined probability of survival. In some embodiments, the method further includes determining a first z-score based on a timed measurement of the biomarker and a second z-score based on the determined rate of change for the biomarker measurements; and wherein determining a severity score further comprises applying the first and second z-scores to a predictive model to generate the severity score. In some embodiments, the method further includes presenting the severity score or the schedule to a human decision-maker via an electronic medical record software system or device.

In another aspect, a computer-implemented is provided to prioritize medical treatment for ToF in a population of human infants, wherein the method includes generating a recommendation for modifying treatment for a set of members in the population who exhibit above-threshold values of a severity score calculated at least in part from the rate of change of an amount of a biomarker determined from a plurality of timed biomarker measurements. In some embodiments of the method, the recommendation for modifying treatment comprises a recommendation for at least one of prioritizing surgical correction, transferring to a particular treatment facility, or ordering additional testing. In some embodiments of the method, the threshold is determined based on survival rates of a reference population of human infants with ToF, and in some embodiments, the threshold is further determined based on available resources for medical treatment. In some embodiments of the method, the severity score is calculated based on a survival prediction model, and in some embodiments, the survival prediction model is used to forecast mortality of members of the population of human infants. In some embodiments, the method further includes presenting the recommendation to a human decision-maker via an electronic medical record software system or device.

In another aspect, a method, or computer readable media having computer-executable instructions embodied thereon for performing a method, is provided for facilitating a method of clinical decision-making, wherein the method includes receiving patient information for a patient including a plurality of timed measurements of a variable associated with a pediatric cardiac condition, and based on the plurality of timed measurements, determining a variable velocity indicative of the rate of change of the measurements of the variable. The method also includes receiving reference information associated with a reference population patients having the pediatric cardiac condition, determining a first z-score based on a timed measurement of the variable and a second z-score based on the determined variable velocity; and applying the first and second z-scores to a prediction model to generate a severity score. The method further includes performing a comparison of the severity score to a threshold; and based on the comparison, determining that the severity score satisfies the threshold, determining medical treatment for the patient. In some embodiments of the method, the threshold is determined based on survival rates of the reference population, and wherein the threshold is determined as satisfied if the severity score exceeds the threshold. In some embodiments of the method, determining medical treatment for the patient comprises designating that the patient is eligible for prioritized medical treatment.

In another aspect, a method, or computer readable media having computer-executable instructions embodied thereon for performing a method, is provided for predicting whether a subject suffering from ToF suffers from a mild or a severe form of ToF, wherein the method includes determining an amount of one or more markers from the group consisting of Brain Natriuretic Peptide (BNP), or N-terminal Brain Natriuretic Peptide (NT-BNP), or pro-NT-BNP, in two or more serial blood, serum, or plasma samples from the subject collected over a period of approximately 60 days or more. The method also includes entering the values into a mathematical model wherein an amount of the marker larger than the reference amount is indicative for a severe form of ToF, and wherein an amount of the marker lower than the reference amount is indicative for a mild form of ToF. In some embodiments, the method further includes determining the relative velocity of BNP rate of change in the serial samples, entering the value(s) into a mathematical model wherein a relative BNP velocity larger than the reference amount of is indicative for a severe form of ToF, and wherein a relative BNP velocity lower than the reference amount is indicative for a mild form of ToF.

In another aspect, a system or device for diagnosing whether a subject suffering from ToF suffers from a mild or a severe form of ToF, is provided wherein the system comprises a component for determining an index or score comprised of log-transformed and z-score-transformed values of biomarkers set forth in claims 1, 2, and 3 the amount of each of the markers determined with a reference amount for each of the markers determined. In some embodiments, the system further includes a component for determining the probability of dying for a subject suffering from ToF while on a waiting list, awaiting the scheduling and performance of corrective surgery.

In another aspect, a method, or computer readable media having computer-executable instructions embodied thereon for performing a method, is provided for determining if a subject suffering from ToF is improving or deteriorating, wherein the method includes comparing a plurality of serial severity scores and survival probabilities determined such as described herein.

Having briefly described an overview of embodiments of the invention, an exemplary operating environment suitable for use in implementing embodiments of the invention is described below.

Turning now to FIG. 1A there is presented an example operating environment 100 suitable for practicing embodiments of the invention. Example operating environment 100 includes a computerized system for compiling and/or running an embodiment of a method for determining TOFI score(s) and for decision support services using the TOFI. With reference to FIG. 1A, one or more electronic health record (EHR) systems, such as hospital EHR system 160, health plan EHR system 162, or ambulatory clinic EHR system 164 are communicatively coupled to network 175, which is communicatively coupled to computer system 120. In some embodiments, components of operating environment 100 that are shown as distinct components may be embodied as part of or within other components of environment 100. For example, the one or more EHR systems 160-164 may be implemented in computer system 120. Similarly, a single EHR system may perform functions for two or more of the example EHR systems shown in FIG. 1A.

In embodiments, network 175 includes the Internet, and/or one or more public networks, private networks, other communications networks such as a cellular network, or similar network(s) for facilitating communication among devices connected through the network. Network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) systems 160, 162, and 164 include one or more data stores of health records, which may be stored on storage 121, and may further include one or more computers or servers that facilitate the storing and retrieval of the health records. In some embodiments, one or more EHR systems 160, 162, and 164 may be implemented as a cloud-based platform or may be distributed across multiple physical locations. EHR systems 160, 162, and 164 may further include record systems, which store real-time or near real-time patient (or user) information, such as wearable, bedside, or in-home patient monitors, for example. Although FIG. 1A depicts multiple example EHR systems, it is contemplated that some embodiments may employ only one EHR system, or alternatively, may rely on surgery scheduling manager 140 and/or provider clinician interface 141 for storing and retrieving patient record information.

Example operating environment 100 further includes provider clinician interface 142 communicatively coupled to the one or more SHRs 160, 162, and 164. Although environment 100 depicts a direct communicative coupling between interface 142 and the one or more SHRs 160, 162, and 164, it is contemplated that some embodiments of interface 142 may be communicatively coupled to the SHRs through network 175. Embodiments of interface 142 may take the form of a user interface operated by a software application or set of applications on a client computing device such as a personal computer, laptop, smartphone, mobile computer, or tablet computing device. In one embodiment, the application includes the PowerChart® software, manufactured by Cerner Corporation. In an embodiment, the application is a Web-based application or applet. Provider clinician interface 142 facilitates accessing and receiving information from a user or health care provider about a specific patient or set of patients for which TOFI assessment and decision support services are to be performed, and facilitates the display of results, recommendations or orders, for example. In some embodiments interface 142 also facilitates receiving orders for the patient from the clinician/user, based on the results. In some embodiments, interface 142 may also be used to display a user interface for receiving information about a patient and displaying results such as illustratively provided in FIG. 10A. Additionally, interface 142 may use used for providing diagnostic services, such as evaluating prediction models discussed in connection to FIG. 2.

Example operating environment 100 further includes computer system 120, which may take the form of a server, and which is communicatively coupled through network 175 to EHR systems 160, 162, and 164, storage 121, and scheduling manager 140.

Embodiments of scheduling manager 140 may take the form of a user interface and application, which may be embodied as a software application operating on one or more mobile computing devices, tablets, smart-phones, front-end terminals in communication with back-end computing systems, laptops or other computing devices. In some embodiments, manager 140 includes a Web-based application or set of applications that is usable to manage user services provided by embodiments of the invention. For example, in some embodiments, manager 140 facilitates scheduling or recommending schedules for surgery, testing, or other orders, which may be based TOFI scores and available resources. In some embodiments, manager 140 is used to display patient information or other information such as illustratively provided in FIGS. 10A and 10B.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120. Some embodiments of software stack 125 include a distributed adaptive agent operating system 129, which may be implemented as a platform in the cloud, and which is capable of hosting a number of services such as 122, 124, 126, and 128. Embodiments of services 122, 124, 126, and 128 run as a local or distributed stack in the cloud, on one or more personal computers or servers such as system 120, and/or a computing device running manager 140. In one embodiment, manager 140 operates in conjunction with software stack 125.

In embodiments, variables indexing service 122 and records/documents ETL service 124 provide services that facilitate retrieving frequent item sets, extracting database records, and cleaning the values of variables in records. For example, variables indexing service 122 may perform functions for synonymic discovery, indexing or mapping variables in records, or mapping disparate health systems' ontologies, such as determining that a particular medication frequency of a first record system is the same as another record system. In some embodiments, these services may invoke software services 126. Software services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org). Software packages 126 are associated with services 128, which include Apache Hadoop and Hbase framework, or similar frameworks operable for providing a distributed file system, and which in some embodiments facilitate provide access to cloud-based services such as those provided by Cerner Healthe Intent®.

Example operating environment 100 also includes storage (or data store) 121, which in some embodiments includes patient data for a candidate patient and information for multiple patients; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, such as for agents/solvers 126, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data stores associated with the one or more EHR systems, such as 161, 162, and 164 and scheduling manager 140. Further, although depicted as a single storage data store, data store 121 may comprise one or more data stores, or may be in the cloud.

Figure 1B:
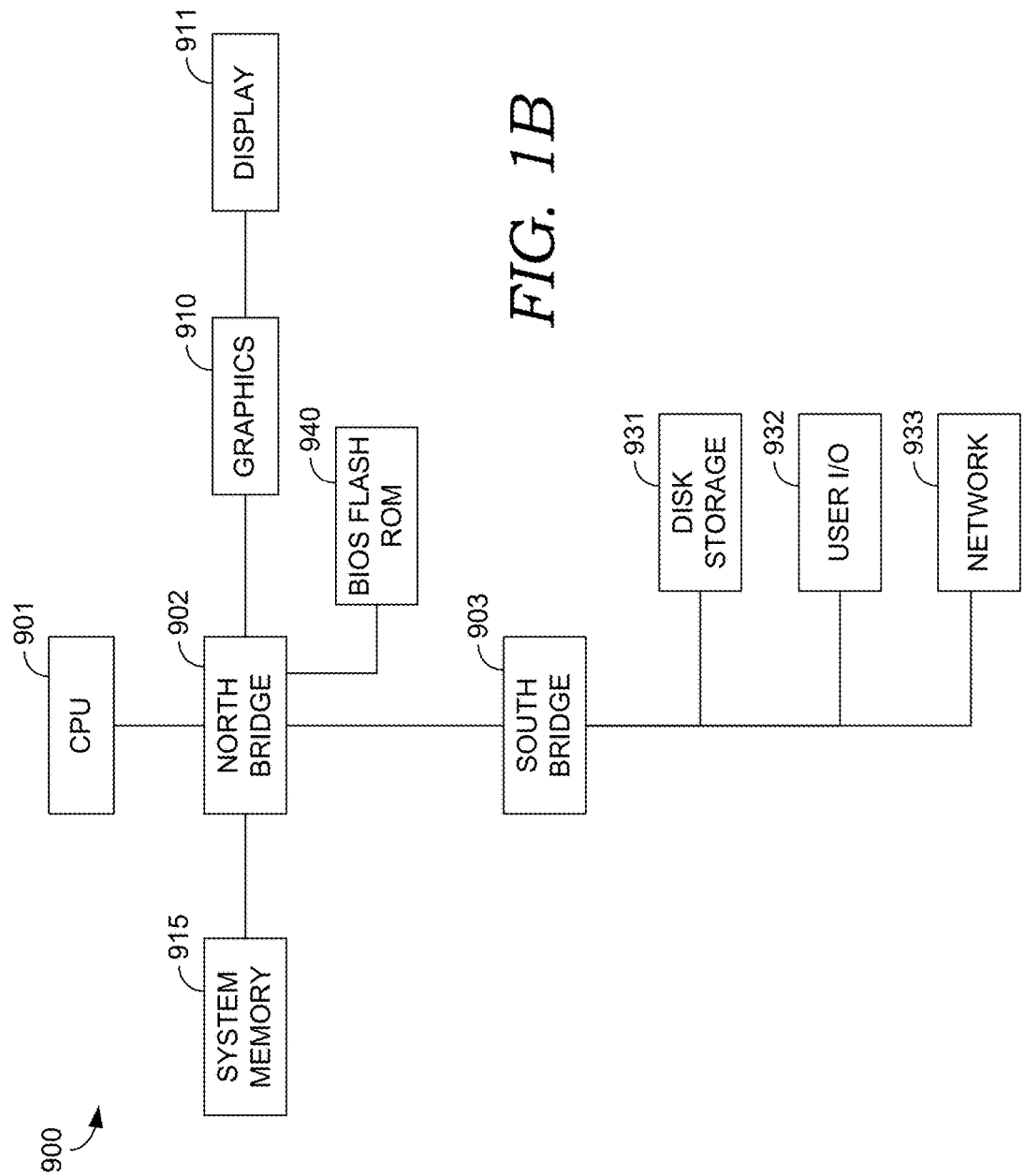

Turning briefly to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

In some embodiments, computer system 120 is a multi-agent computer system with agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy. Additional information about the capabilities and functionality of agents and distributed multi-agent operating systems, as they relate to these embodiments, is provided in U.S. patent application Ser. No. 13/250,072, filed on Sep. 30, 2011, which is herein incorporated by reference in its entirety.

Figure 2:
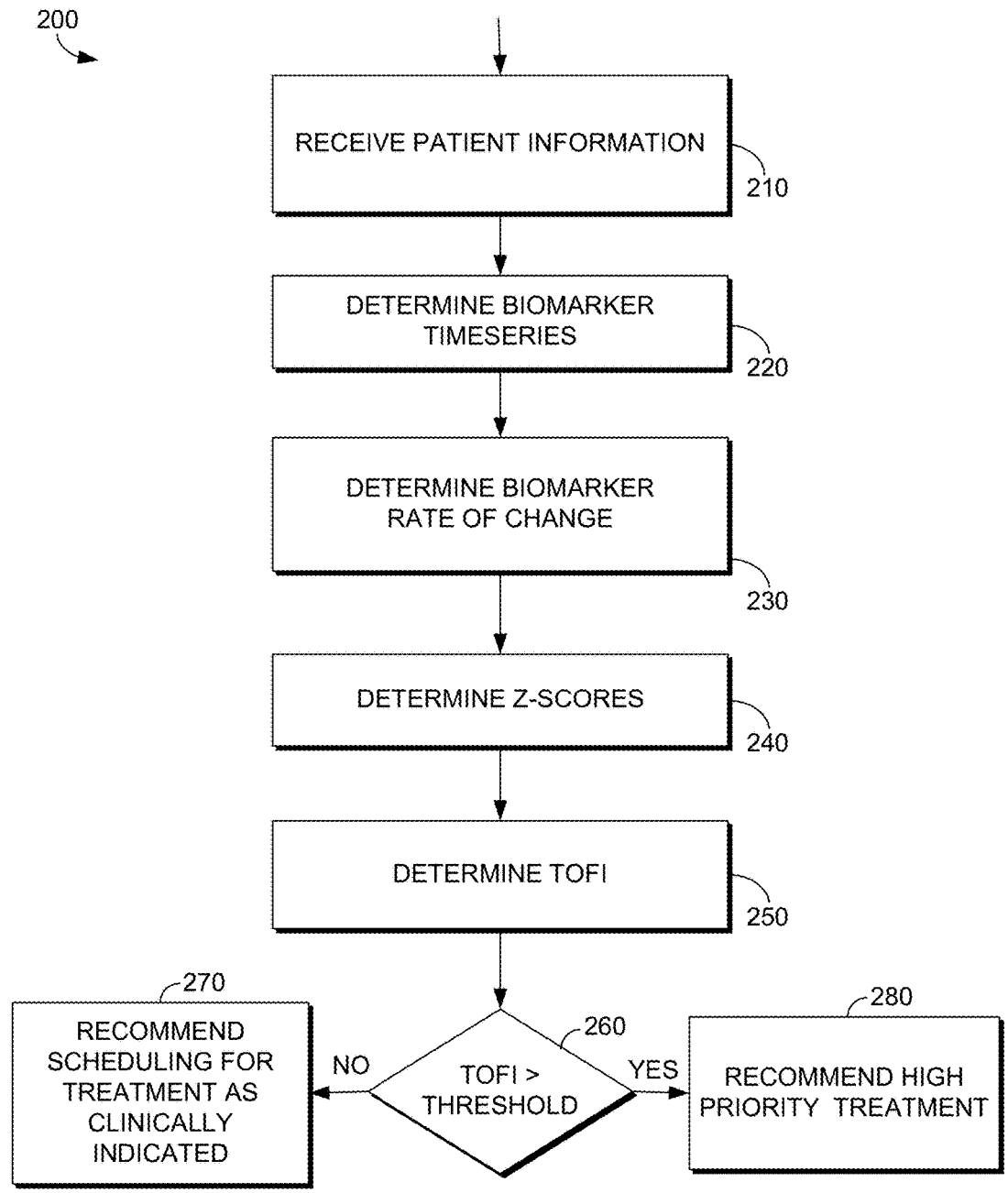
FIG. 2 depicts a flow diagram of a method for determining ToF severity which may be used for triaging, in accordance with embodiments of the present invention.

Turning now to FIG. 2, a flow diagram is provided for an embodiment of a method for determining TOF severity, which may be used for triaging by determining probable survival times and/or managing treatment including the scheduling surgery, transfers, or other orders, and referred to generally herein as method 200.

With reference to FIG. 2, embodiments of method 200 provide a predictive model. In some embodiments, the model can use a reduced number of variables but still have accuracy sufficient for N-of-1 individual patient predictions. Furthermore, in some embodiments, variables in the model are not so exotic as to require admitting the patient into an academic hospital, tertiary center, or otherwise perform elaborate, extensive, or invasive testing. Rather the non-exotic variables are able to be readily obtained by typical community-type hospitals or centers, such as by means of a simple body-fluid sample, thereby allowing triage to take place sooner, cheaper, and/or closer to where a patient's family lives. In some embodiments, the predictive power of the model is primarily or solely based on two variables: a Z-score transformed level or a first biomarker and the relative velocity of the biomarker (at times referred to herein as SDS1 and SDS2, respectively, and described further in connection to a step 240).

Embodiments of method 200 described below use BNP as a biomarker, although other biomarkers are contemplated within the scope of the invention. Further, some embodiments of the predictive model may use multiple variables, and some embodiments may form a composite biomarker from multiple variables. For example, BNP levels and the times from birth at which the BNP levels were determined, or relative BNP velocity and measured (or otherwise determined) amount of right-to-left shunt (L-R shunt) flow. In particular, patients having L-R shunt show an increase in BNP, which leaks into the blood plasma, which can make it a suitable biomarker for failing left ventricle.

Continuing with FIG. 2, at a step 210 of method 200, receive patient information for candidate patient. Embodiments of step 210 include receiving patient information and biomarker information from the patient. In some embodiments this information includes the patient's EHR or information about the patient such as the patient's age, condition, or history and biomarker data such as biomarker amount(s) (or variable level for composite biomarkers) and time(s) the amount was measured. For example, in some embodiments of step 210, information regarding two or more biomarker levels, corresponding to different times, for a pediatric patient are received. In one embodiment, the time difference between when the different times spans at least approximately 60 days or more. In some embodiments the biomarker information (such as one or more timed BNP, N-terminal BNP (NT BNP) or pro-NT-BNP levels) may be received from the patient's EHR or from biological samples, such as blood or body-fluid sample(s) at sufficient levels to measure, or a combination of EHR information and biological sample(s), and may be received from a patient in utero, depending on the specific biomarker. In some embodiments, a caregiver or clinician provides biomarker information for the patient, such as by entering it into a user interface like user interface 1010 illustratively depicted in FIG. 10A. In some embodiments one or more software agents or routines provides the biomarker information, such as by accessing the patient's EHR or testing results. In some embodiments, the amount of biomarker is determined via an immunoassay.

At a step 220, a biomarker timeseries is determined. In some embodiments, information from at least two biomarker levels or amounts, and time of measurement are determined thereby comprising a timeseries of two entities, such as biomarker-amount B1 at time t1 and biomarker-amount B2 at time t2, where t1 and t2 represent the patient's approximate age, such as in days, or a date or time that can be used to determine the patient's age at the time corresponding to the biomarker amount, for example. In some embodiments a selection from a plurality of timed biomarker amounts is performed for biomarker values obtained from the patient over a period of time. In some embodiments, this period of time is several weeks or months, based on known survival rates for patients having TOF. For example, in some embodiments, step 220 comprises selecting a plurality of BNP values (in pg/ml) that have been determined from blood sample specimens obtained from the patient over a time period of 60 days or more.

At a step 230, the rate of change for the biomarker is determined. In some embodiments, the rate of change comprises a velocity of the biomarker amount or the slope of the biomarker timeseries values determined in step 220. For example, a BNP velocity given as change in pg/mL/month.

In some embodiments, step 230 comprises determining a relative rate of change (or relative velocity). For example, some biomarker amounts (or levels of variables used for composite biomarkers) change more drastically as time from birth increases, thus variations in the timing of when biomarker amount (or variable level) is determined can result in skewed data making it difficult to compare patients. Accordingly, some embodiments use a relative rate of change (or relative velocity), which may be obtained, for example, by dividing the velocity in arrears by the most recent or current value. Embodiments of step 230 may calculate the biomarker velocity in ways other than determining the slope as known in the art. Moreover, in some embodiments, instead of relative velocity, biomarker doubling rate may be used, and in some embodiments, such as where a larger cohort exists with more controlled sampling times for the biomarker or variables, absolute velocity can be used.

At step 240, standard scores or z-scores are determined based on the biomarker values and biomarker velocity. Some embodiments of step 240 comprise performing a logarithmic transformation of a raw biomarker value, which may be received in step 210, and the relative biomarker velocity, determined in step 230, and then subtracting from each the mean and dividing by the standard deviation. For example, for a biomarker B, $ln(B)-B_{mean}/B_{Stdev}$ and $ln(Bvel)-Bvel_{mean}/Bvel_{StDev}$. Or, using actual values of the BNP biomarker from the embodiments discussed in connection to the data in FIGS. 4-10 and in particular the data presented in FIG. 9B: SDS1=max(0,(ln(BNP)−4.3/0.56, wherein 4.3 is the mean and 0.56 is the standard deviation for BNP; and SDS2=max(0,(ln(BNPvelocity/BNP)−2.8/0.64, where 2.8 and 0.64 are the mean and standard deviation, respectively, and BNPvelocity/BNP is the relative velocity. Accordingly, SDS1 is the z-score for the biomarker (here BNP) and SDS2 is the z-score for the relative velocity of the same biomarker. In some embodiments, such as shown in the two preceding examples, SDS1 or SDS2 are set equal to zero where they're values would otherwise be determined as negative.

At a step 250, a Tetralogy of Fallot Index (TOFI) score is determined. In some embodiments, the standard scores or z scores determined at step 240 are combined using a predictive model, for example a time-to-event survival model, to obtain a TOFI score, which can be used to determine a predicted mortality likelihood. The predictive model may comprises a Cox Proportional Hazards model wherein a probability of survival over a time interval t can be determined as $S(t)=S_0(t)^{exp(TOFI-\mu)}$, in some embodiments, wherein TOFI can be determined as TOFI=β1 SDS1+β2 SDS2, μ is the population-mean TOFI score, and $S_0(t)$ is a default survival rate, which may be received from an appropriate cohort determined from a health database, such as Cerner Health Facts® data warehouse, an EMR-derived database, or a nation-wide information on survival rate for patients having TOF. In some embodiments, $S_0(t)$ is determined from historical data, and may be provided by a caregiver or clinician, or referenced, or hard-coded into, a software routine or solver library used by a software agent. In some embodiments, TOFI coefficients can be determined as shown in the algorithm provided in FIG. 9D based on the data provided in FIGS. 9B and 9C, where coefficients β1 and β2 are determined as 2.139 (rounded to 2.14) and 1.117 (rounded to 1.12) for SDS1 and SDS2, respectively. Thus, here TOFI is determined as TOFI=2.14×SDS1+1.12×SDS2. In this example, the population-mean TOFI score, determined from a heart failure cohort in the proportional hazards model, is 1.013. Thus, $S(t)=S_0(t)^{exp(TOFI-1.013)}$. Some embodiments of step 250 therefore may include receiving parameters for the prediction model and/or receiving $S_0(t)$ values. An example survival curve for selected TOFI score values is provided in FIG. 7B, which is described in greater detail below.

In some embodiments, other suitable predictive models may be used. The Cox regression model is often used for analyzing prognostic factors in clinical research probably because the model allows for estimating and making inferences about the parameters without assuming any distribution for the lifetime, whose distribution is often unknown. However, in some cases the model has the requirement of proportional hazards, which may not always be satisfied by the data. Parametric models (such as Log-normal, Log-logistic, Weibull, Exponential, and Accelerated Failure Time models) may provide an alternative framework to fit the data. Moreover, embodiments using these models would measure the direct effect of the explanatory variables on the survival time and not on a conditional probability, as can be done in the Cox regression model. This characteristic allows for an easier interpretation of the results because the parameters measure the effect of the correspondent covariate on the mean lifetime. Examples of other models include: other proportional hazards models; parametric models including Log-normal, Log-logistic, Weibull, Exponential, and the accelerated failure model (AFT), which can be framed as linear models for the logarithm of the survival time; gamma frailty model; or other suitable predictive, time-to-event, or survival models known in the art such as those taught in Survival Analysis—Techniques for Censored and Truncated Data, by Klein, J. and M. Moeschberger (Springer, 1997) which is herein incorporated by reference. In some embodiments, the predictive model may be determined based on desired sensitivity, available reference data, which may be used to determine parameters of the model, and/or the biomarker(s).

At a step 260, the TOFI score is evaluated to determine a severity of the patient's condition, which may be used for determining whether the patient should be recommended for high priority treatment (step 280) or scheduled for treatment as clinically indicated (step 270). In some embodiments, step 260 comprises performing a comparison of the TOFI against a threshold, wherein when the threshold is exceeded, the patient is determined as having severity warranting higher priority treatment and the method proceeds to step 280. Where the threshold is not exceeded, at a step 270, the patient maybe scheduled for treatment as clinically indicated. In some embodiments, not exceeding the threshold indicates that the patient's condition is not severe enough to warrant high priority treatment (step 280), such as urgent scheduling for surgical correction, transfer to an appropriate or available treatment facility, or additional testing. In some embodiments, step 260 also comprises evaluating whether the TOFI model-predicted mortality risk or survival likelihood is acceptable, should the patient be retained on a surgery waiting list and surgical treatment deferred. In some embodiments, this includes determining an appropriate length of wait time for surgery for a patient or predicting survival probability for having to wait to a future date. In some embodiments, an estimated treatment cost may be determined for prioritizing patient treatment or for deferring treatment.

In some embodiments, the TOFI score is determined to indicate the severity of the patient's condition. For example a higher TOFI score indicates a more severe condition requiring more urgent treatment, and the threshold is set as a decision point such that patient's having TOFI scores higher than the threshold are deemed to require priority treatment. Thus in some embodiments, the threshold decision point is based on the available resources (including costs and treatment facilities), the number of patients requiring treatment, and the survival times of the patients. For example, the threshold may be set higher, if the available treatment resources are limited such that only the most severe cases should receive priority. In some embodiments, the threshold is set as 1 to be consistent with other similar decision-point thresholds for surgery or determining priority, such as the Model For End-Stage Liver Disease (MELD) score used to determine liver transplant priority. Thus caregivers may be more inclined to rely on embodiments of the present invention using a threshold of 1 because of their familiarity with other models having a threshold of 1. In some of these embodiments where the threshold is set to 1, the TOFI scores may be adjusted such that the threshold remains 1 but is will still sufficiently discriminate those patients needing priority treatment. In other words, rather than adjusting the threshold as needed based on available resources, number of patients requiring treatment, and the survival times of the patients, the TOFI scores can be adjusted. In some embodiments, the threshold is determined by a caregiver or a clinician, an insurance provider, or a software agent or program routine, which may determine or recommend a threshold decision point based on available resources, the number of patients requiring treatment, survival times of the patients, and/or likelihood of success for intervening treatments that may defer treatment for some patients. Additional details regarding determining the threshold decision point (or cut point) are described in connection with FIG. 9A.

In some embodiments, step 260 comprises rank-ordering patients on a waiting list for treatment based on determined TOFI scores of the patients, for example, such that patients with a higher TOFI score have a higher rank and patients with a lower TOFI score have a lower rank. In some embodiments, treatment of the patients, such as surgical correction, transfer, testing, or other treatment is automatically scheduled, rescheduled, or recommended for scheduling or rescheduling, based on the TOFI scores, available resources, and/or number of patients. In some embodiments, patients are recommended for priority treatment, wherein the recommendation may be provided by a user interface, such as clinician interface 142.

Figure 3A:
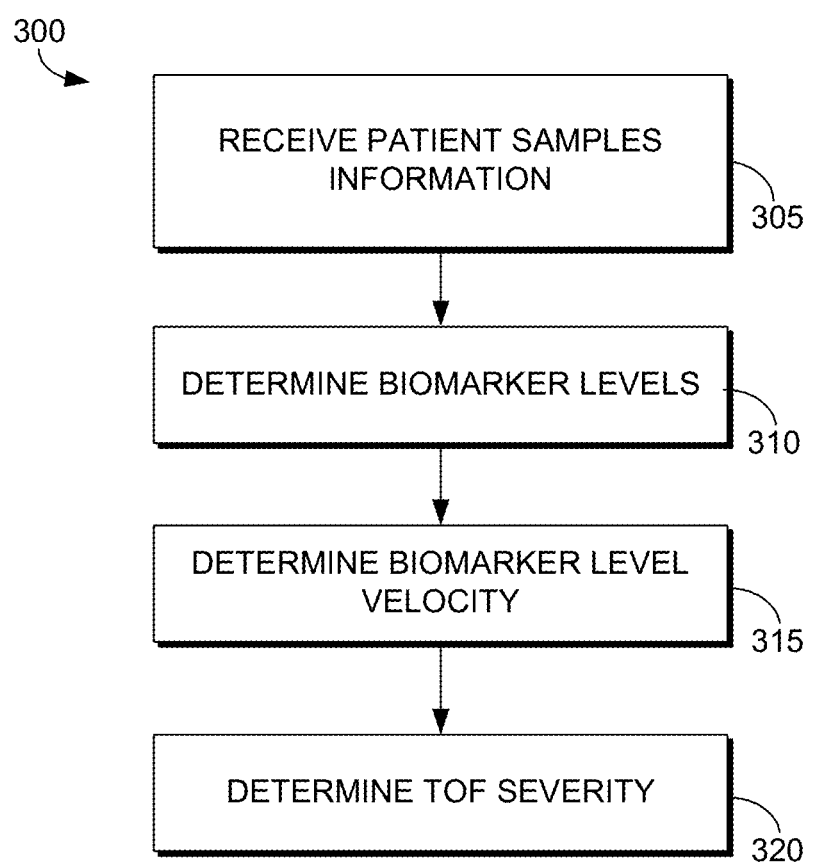
FIGS. 3A and 3B, provide flow diagrams of method for monitoring a person having ToF.

Turning now to FIG. 3A, a flow diagram is provided which illustrates an embodiment of a method for monitoring a person having ToF and referred to generally herein as method 300. At step 305 patient samples information is received corresponding to two or more samples at different times. In some embodiments, patient samples information comprises receiving timed information about a two or more biological samples from the same patient, wherein each biological sample obtained at a different time. The biological sample may comprise blood, serum, plasma or other bodily fluid from the patient. In some embodiments, patient samples information includes timed information measured from the patient such as determined by one or more probes or sensors or previously determined information about the patient from the patient's health record.

At step 310, an amount of biomarker is determined in the two or more biological samples. In some embodiments, step 310 may already be determined, such as where the patient samples information includes information measured from the patient. In one embodiment, the amount of biomarker is determined via an immunoassay.

At step 315, a velocity or slope of the biomarker is then determined. In some embodiments, velocity is determined such as described at step 230 of method 200, in connection to FIG. 2. In one embodiment, the velocity is determined by the rate of change in pg/mL/month of the amount of biomarker.

Figures 7A, 7B:
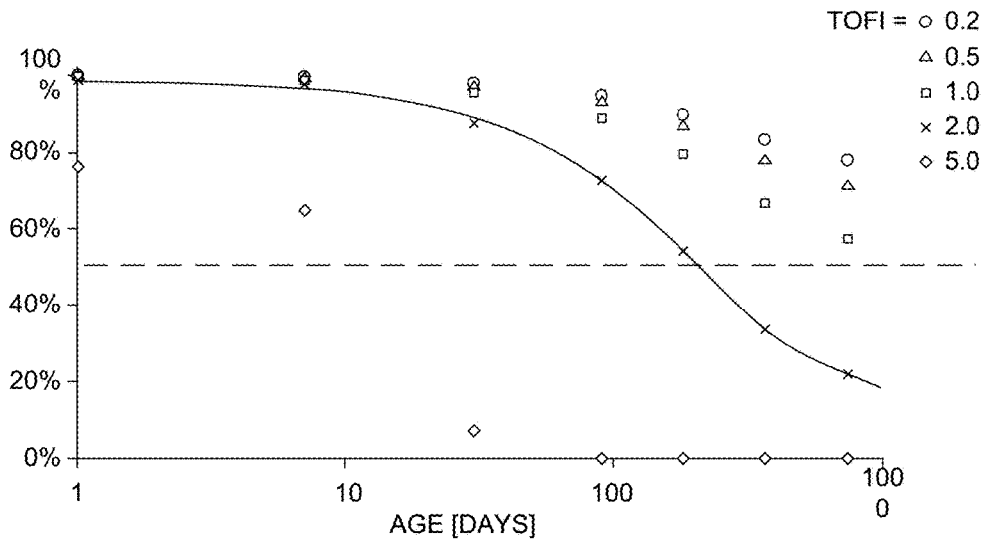
FIG. 7A provides a table of representative TOFI score values determined in accordance with an embodiment of the present invention.
FIG. 7B illustratively depicts example survival curves for the TOFI score values from the table of FIG. 7A, and determined in accordance with an embodiment of the present invention.

At step 320, the velocity determined in step 315 is compared to control velocities and the severity of ToF is determined. In some embodiments, the control velocities are determined based on the survival curve for selected Tetralogy of Fallot Index (TOFI score) values, such as illustrated in FIGS. 7A and 7B. In some embodiments, the severity of ToF is determined based on the TOFI score of the patient where a higher TOFI score indicates more severity of the ToF. In some embodiments, step 320 comprises determining ToF severity by determining a TOFI score for the patient as described in steps 240-260 of method 200, in connection to FIG. 2.

Figure 3B:
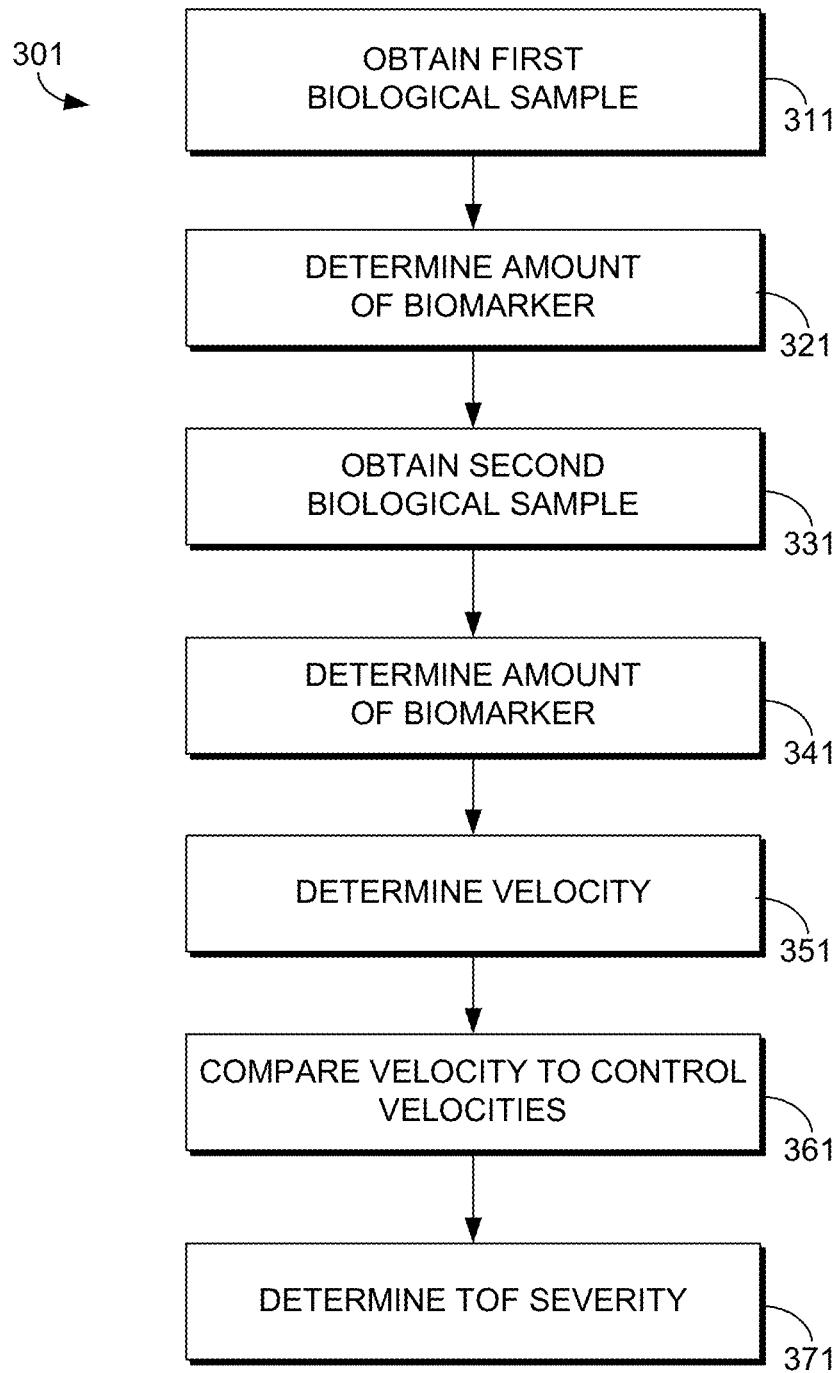

Turning now to FIG. 3B, a flow diagram is provided which illustrates an embodiment of a method for monitoring a person having ToF and referred to generally herein as method 301. At step 311 a first biological sample is obtained from the patient. In one embodiment, a biological sample comprises any biological sample that contains Brain Natriuretic Peptide (BNP), N-terminal Brain Natriuretic Peptide (NT-BNP), or pro-NT-BNP at sufficient levels to measure, such as blood, serum, and/or plasma from the patient. In another embodiment, the biological sample is another bodily fluid from the patient. In some embodiments, the biological sample from the patient includes timed information measured from the patient such as determined by one or more probes or sensors or previously determined information about the patient from the patient's health record.

At step 321, the amount of a biomarker in the first biological sample is determined, wherein the biomarker comprises one or more of BNP, NT-BNP, or pro-NT-BNP. In one embodiment, the amount of biomarker is determined via an immunoassay. In some embodiments, the biomarker information (such as timed BNP levels) may be received from the patient's EHR, blood or body-fluid sample(s), or a combination, and may be received from a patient in utero, depending on the specific biomarker. In another embodiment, a caregiver or clinician provides biomarker information for the patient, such as by entering it into a user interface like user interface 1001 illustratively depicted in FIG. 10A. In some embodiments, one or more software agents or routines provides the biomarker information, such as by accessing the patient's EHR or testing results.

At step 331, a second biological sample is obtained from the same patient at a later time than the first biological sample. In one embodiment, the second biological sample comprises any biological sample that contains Brain Natriuretic Peptide (BNP), N-terminal Brain Natriuretic Peptide (NT-BNP), or pro-NT-BNP at sufficient levels to measure, such as blood, serum, and/or plasma from the patient. In another embodiment, the biological sample is another bodily fluid from the patient. In some embodiments, the biological sample from the patient includes timed information measured from the patient such as determined by one or more probes or sensors or previously determined information about the patient from the patient's health record. In one embodiment, the time difference between when the first and second biological samples are obtained comprises approximately 60 days or more.

At step 341, the amount of a biomarker in the second biological sample is determined, wherein the biomarker comprises one or more of BNP, NT-BNP, or pro-NT-BNP. In one embodiment, the amount of biomarker is determined via an immunoassay. In some embodiments, the biomarker information (such as timed BNP levels) may be received from the patient's EHR, blood or body-fluid sample(s), or a combination, and may be received from a patient in utero, depending on the specific biomarker. In another embodiment, a caregiver or clinician provides biomarker information for the patient, such as by entering it into a user interface like user interface 1010 illustratively depicted in FIG. 10A. In some embodiments, one or more software agents or routines provides the biomarker information, such as by accessing the patient's EHR or testing results.

At step 351, the velocity of the biomarker amount is then determined for the patient. The velocity of the one or more of BNP, NT-BNP, or pro-NT-BNP markers may be determined for two or more biological samples from the same patient. In some embodiments, the velocity may be determined such as described in step 230 of method 200, in connection to FIG. 2. In one embodiment, the velocity is determined as the rate of change in pg/mL/month of the amount of biomarker.

At step 361, the velocity determined in step 351 from the patient is compared to the control velocities. In one embodiment the control velocities are determined based on a survival curve for selected Tetralogy of Fallot Index (TOFI score) values as determined from a reference population and such as illustrated in FIGS. 7A and 7B.

At step 371, the severity of the ToF is determined. In some embodiments, step 371 comprises determining ToF severity by determining a TOFI score for the patient such as described in steps 240-260 of method 200, in connection to FIG. 2. In some embodiments, when the patient's TOFI score is 1.0 or less, there is not a requirement for urgent corrective surgery. As previously mentioned, in some embodiments, the TOFI score is evaluated to determine a severity of the patient's condition, which may be used for determining whether the patient should be recommended for high priority treatment or scheduled for treatment as clinically indicated, such as described in steps 260-280 of method 200. In some embodiments, not exceeding the threshold indicates that the patient's condition is not severe enough to warrant high priority treatment, such as urgent scheduling for surgical correction, transfer to an appropriate or available treatment facility, or additional testing.

In some embodiments, step 371 also comprises evaluating whether the patient be retained on a surgery waiting list and surgical treatment deferred, based on the determined severity. In some embodiments, this includes determining an appropriate length of wait time for surgery for a patient or predicting survival probability for having to wait to a future date. In some embodiments, an estimated treatment cost may be determined for prioritizing patient treatment or for deferring treatment.

Figure 3C:
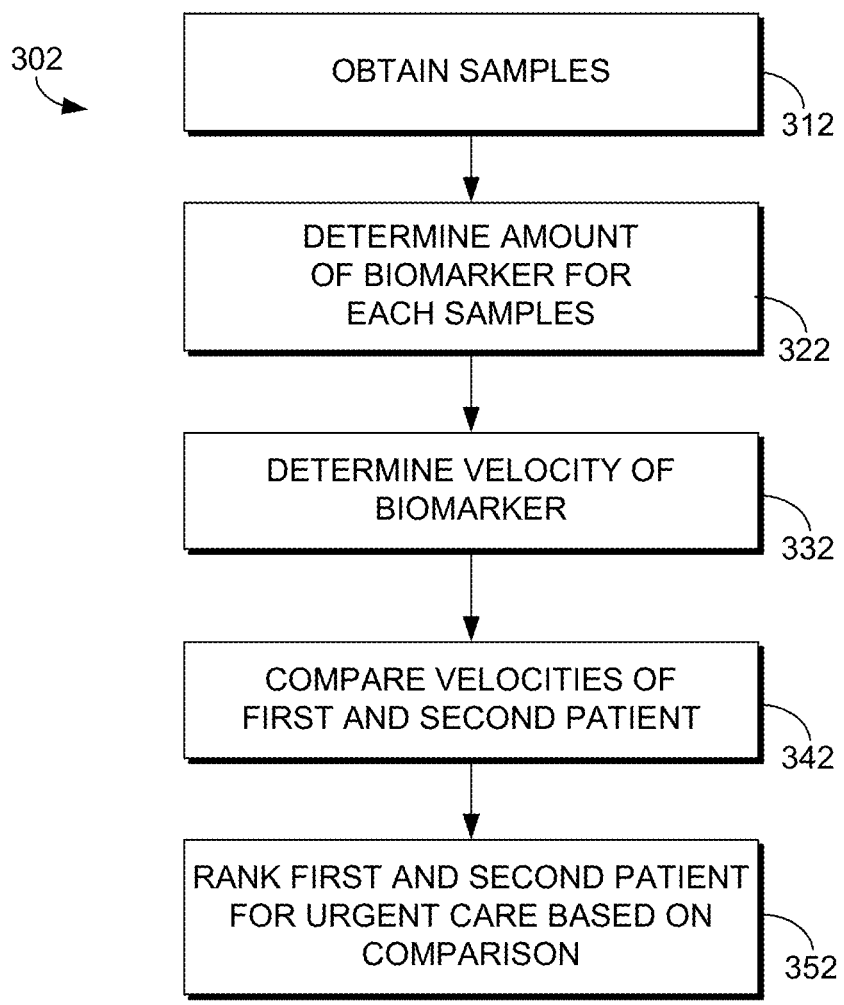
FIG. 3C provides a flow diagrams of a method of ranking ToF patients that require medical treatment for the ToF, in accordance with embodiments of the present invention.

Turning now to FIG. 3C, a flow diagram is provided which illustrates an embodiment of a method for ranking ToF patients that require medical treatment for the ToF and which is referred to generally herein as method 302. At step 312 biological samples are obtained from a first patient and a second patient. In some embodiments, biological samples are obtained from a plurality of patients. In some embodiments, each sample is associated with a time at which it was obtained from the patient. In some embodiment, biological samples comprise any biological sample in which Brain Natriuretic Peptide (BNP), N-terminal Brain Natriuretic Peptide (NT-BNP), or pro-NT-BNP can be detected, such as blood, serum and/or plasma from a patient. In another embodiment, the biological sample is another bodily fluid from the patient. In some embodiments, the biological sample from each patient includes timed information measured from the patient such as determined by one or more probes or sensors or previously determined information about the patient from the patient's health record.

At step 322, the amount of biomarker in each of the patients' biological samples is determined. In some embodiments, step 322 may already be determined, such as where the patient samples information includes information measured from the patient or from a patient's health record. In one embodiment, the amount of biomarker is determined using an immunoassay. In some embodiments the biomarker information (such as timed BNP levels) may be received from the patient's EHR, blood or body-fluid sample(s), or a combination, and may be received from a patient in utero, depending on the specific biomarker. In some embodiments, a caregiver or clinician provides biomarker information for the patient, such as by entering it into a user interface like user interface 1010 illustratively depicted in FIG. 10A. In some embodiments one or more software agents or routines determines the biomarker information, such as from the patient's EHR or testing results. In one embodiment, the biomarker comprises one or more of BNP, NT-BNP, and pro-NT-BNP. In one embodiment, the biomarker comprises one or more of BNP, NT-BNP, and pro-NT-BNP, lactic acid, cardiac index, right atrial pressure, central venous pressure, right ventricular ejection fraction, rapid shallow breathing index (Tobin score), ratio of VSD shunt flow to systemic flow, and right-to-left shunt flow.

At step 332, a velocity or slope of the biomarker for each of the patients is then determined. In some embodiments, velocity is determined such as described at step 230 of method 200, in connection to FIG. 2. In some embodiments, the velocity is determined by the rate of change in pg/mL/month of the amount of the biomarker.

At step 342, the velocity of the first patient's biomarker and the velocity of the second patient's biomarker are compared to each other. In one embodiment, the velocity of a plurality of patients is compared.

At step 352, the patients are ranked for medical treatment (such as urgent care or priority scheduling) based on the comparison of the velocities. In one embodiment, the ranking is based on a numbering system in which a higher number corresponds to a more urgent need for medical treatment of the ToF. In some embodiments, the numbering system is based on a survival prediction model, such as described in steps 240 and 250 of method 200, and in some embodiments comprises a score. In some embodiments, the score is determined based on biomarker values and velocities as determined from a reference population, such as illustrated in FIGS. 7A and 7B. In some embodiments, step 352 comprises ranking the patients by determining a TOFI score for the patients as described in steps 240-260 of method 200. In some embodiments, when the patient's TOFI score is 1.0 or less, there is not a requirement for urgent corrective surgery.

In some embodiments, step 352 comprises rank-ordering the patients on a waiting list for treatment based on the determined scores, for example, such that patients with a higher TOFI score have a higher rank and patients with a lower TOFI score have a lower rank. In some embodiments, step 352 also comprises evaluating whether the patient be retained on a surgery waiting list and surgical treatment deferred, based on the determined severity. In some embodiments, this includes determining an appropriate length of wait time for surgery for a patient or predicting survival probability for having to wait to a future date. In some embodiments, an estimated treatment cost may be determined for prioritizing patient treatment or for deferring treatment.

With reference to FIGS. 2 and 3A-3C, in some embodiments of the invention, there is a method of determining if a ToF patient is eligible for urgent surgical correction. In this embodiment, the velocity of one or more biomarkers of Brain Natriuretic Peptide (BNP), N-terminal Brain Natriuretic Peptide (NT-BNP), or pro-NT-BNP from a biological sample from a patient is obtained. In one embodiment, the velocity is determined by the rate of change in pg/mL/month of the amount of biomarker. Biological samples comprise any biological sample in which Brain Natriuretic Peptide (BNP), N-terminal Brain Natriuretic Peptide (NT-BNP), or pro-NT-BNP can be detected, such as blood, serum and plasma. Next, the velocity of the one or more of BNP, NT-BNP, or pro-NT-BNP of the biological sample is compared to control velocity measurements. In one embodiment the control velocities are determined based on the survival curve for selected Tetralogy of Fallot Index (TOFI score) values as illustrated in FIG. 7. The amount of one or more markers of lactic acid, cardiac index, right atrial pressure, central venous pressure, right ventricular ejection fraction, rapid shallow breathing index (Tobin score), ratio of VSD shunt flow to systemic flow, and right-to-left shunt flow from a biological sample from a patient is then determined. The amount of each of the markers is then compared to a reference amount for each of the markers determined. Subsequently, it is determined if the patient is eligible for urgent surgery based on results of the comparison of the biomarkers and the comparison of the markers.

In one embodiment, a method for determining if a subject suffering from ToF is eligible for urgent surgical correction comprises determining an amount of one or more markers from the group consisting of BNP, or NT-BNP, or pro-NT-BNP, lactic acid, and, optionally, one or more markers from the group cardiac index (in $L/min/m^2$), right atrial pressure, central venous pressure, right ventricular ejection fraction, rapid shallow breathing index (Tobin score), ratio of VSD shunt flow to systemic flow, and right-to-left shunt flow, comparing the amount of each of the markers determined with a reference amount for each of the markers determined, and determining if the subject is eligible for urgent surgery based on the results of the comparison step.

With reference to FIGS. 4-10, embodiments of the present invention have been reduced to practice using computer system 120 comprising a server cluster running the Linux operating system on a multi-agent computing platform, and Discern distributed adaptive knowledge operating system (DAAKOS) agent solver implementing the Cox Proportional Hazards model where the coefficients of the equation calculated by the solver agent were derived from a cohort of ToF patients retrieved from Cerner's Health Facts® EMR-derived, HIPAA confidentiality-protected data warehouse.

Figure 4A:
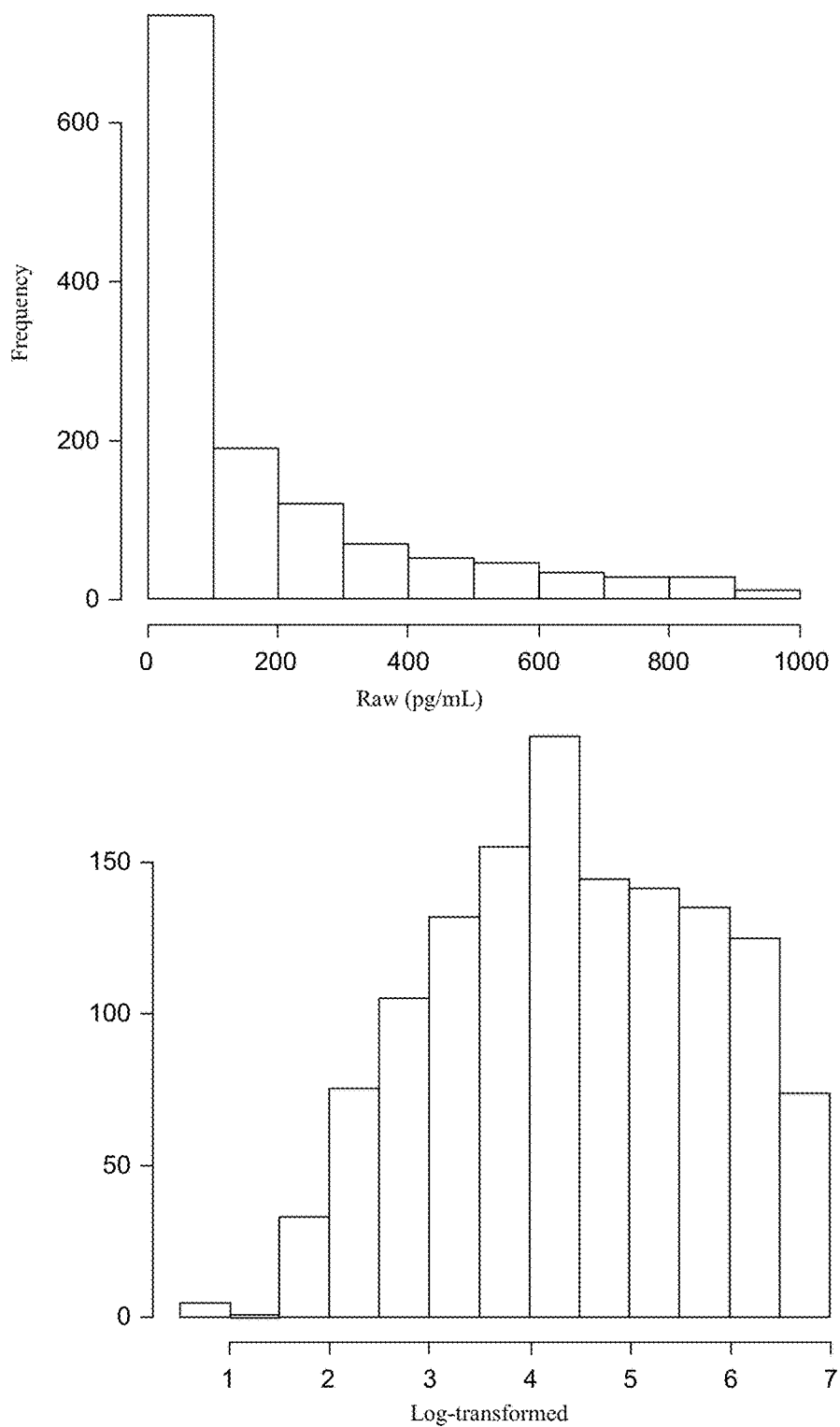
FIGS. 4A and 4B illustratively depicts raw values and Log-transformed values of plasma BNP (in pg/mL) from a cohort of 4,360 ToF patients.
Figure 4B:
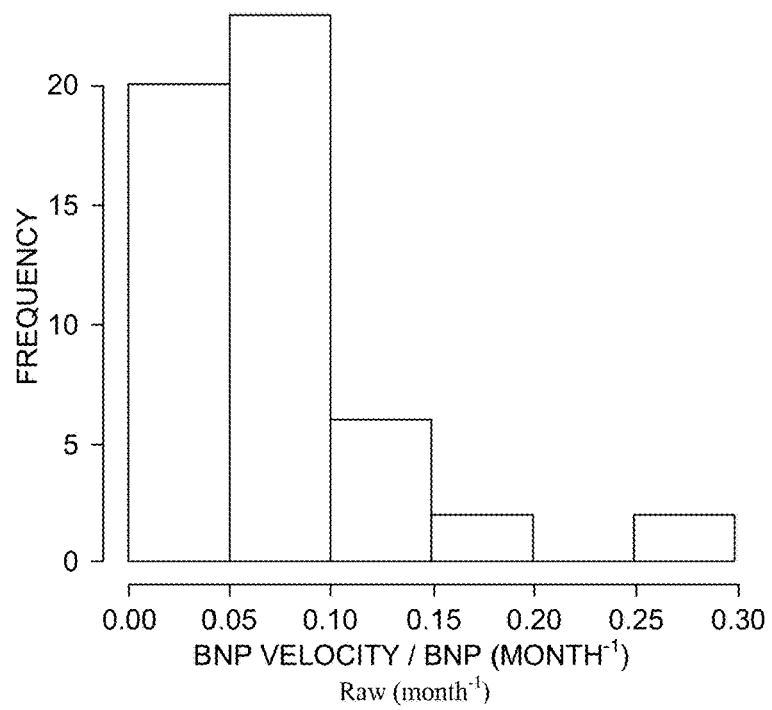
Figure 4B:
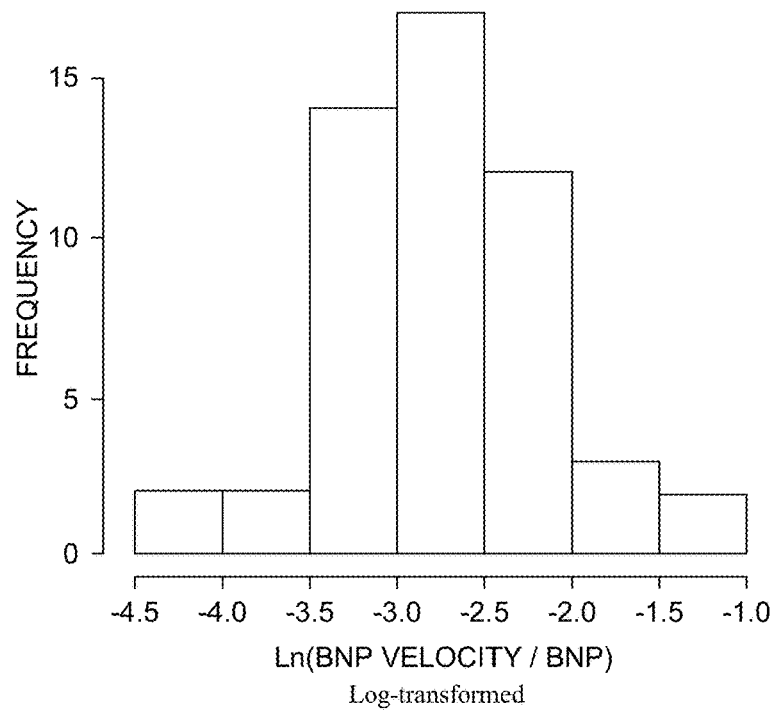

Turning now to FIGS. 4A-B, FIG. 4A illustratively depicts raw values (top graph) and Log-transformed values (bottom graph) of plasma BNP (in pg/mL) from a cohort of 4,360 ToF patients (subset aged 0 to 35 months) retrieved from Cerner's EMR-derived Health Facts® data warehouse, incident upon the source institutions between Jan. 1, 2000, and Dec. 31, 2012. Logarithmic transformation of the values substantially reduces the right-skewedness of the original statistical distribution. FIG. 4B illustratively depicts raw (top graph) and Log-transformed values (bottom graph) of relative BNP velocity (in $month^{-1}$) for a sub-cohort of 51 ToF patients retrieved from Cerner's EMR-derived U.S.-based Health Facts® data warehouse, incident upon the source institutions between Jan. 1, 2000, and Dec. 31, 2012, who had four or more serial determinations of plasma BNP from which velocity could be calculated and a relative velocity with respect to the then-current BNP level could be derived.

Figure 5:
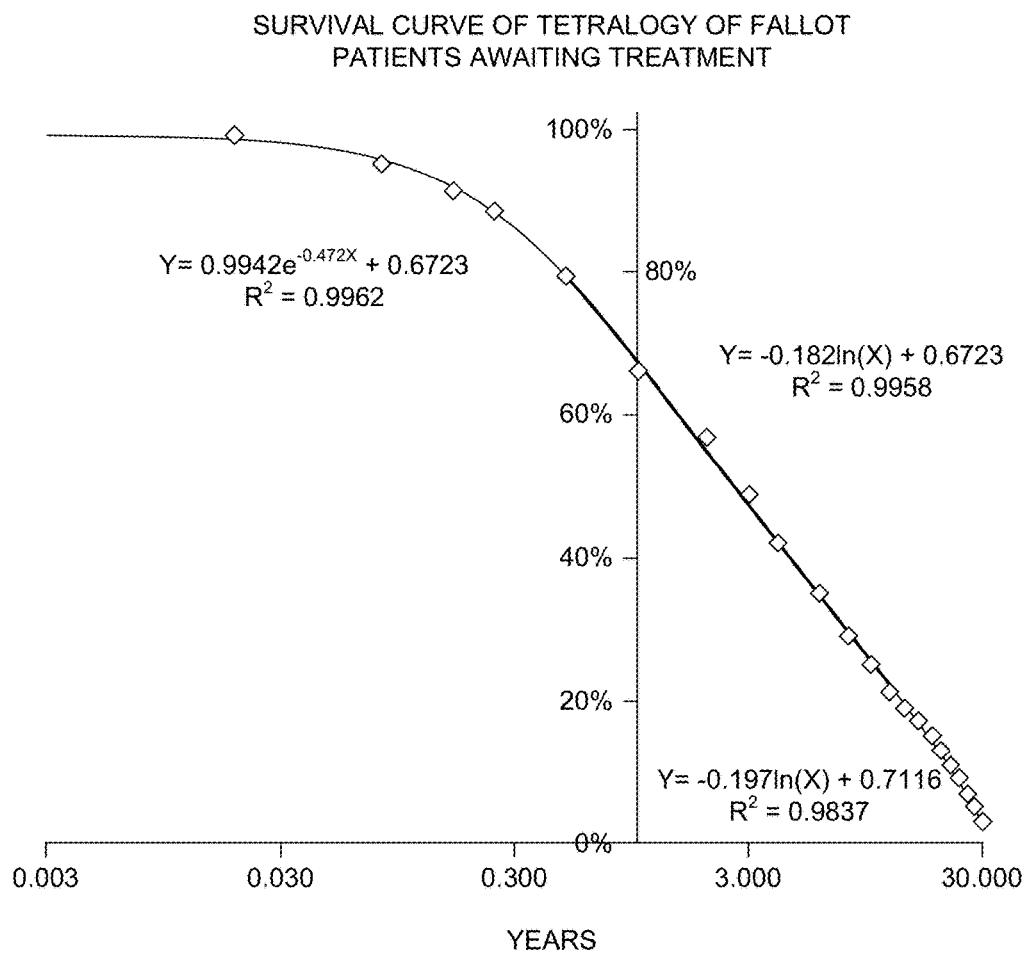
FIG. 5 illustratively depicts survival curves for patients having ToF.

FIG. 5 illustratively depicts survival curves for the Health Facts® cohort of ToF patients superimposed upon the survival data for untreated ToF patients as published by Bertranou, Blackstone, and Kirklin in 1978. Here, the X-axis is years (logarithmic) and Y-axis is survival rate. From these superimposed survival curves, it can be seen that the untreated survival rates determined from the Health Facts® cohort of TOF patients is approximately the same as that determined in the Kirklin study from 1978. For example, nearly 30% of untreated patients will die within the first year.

Figure 6:
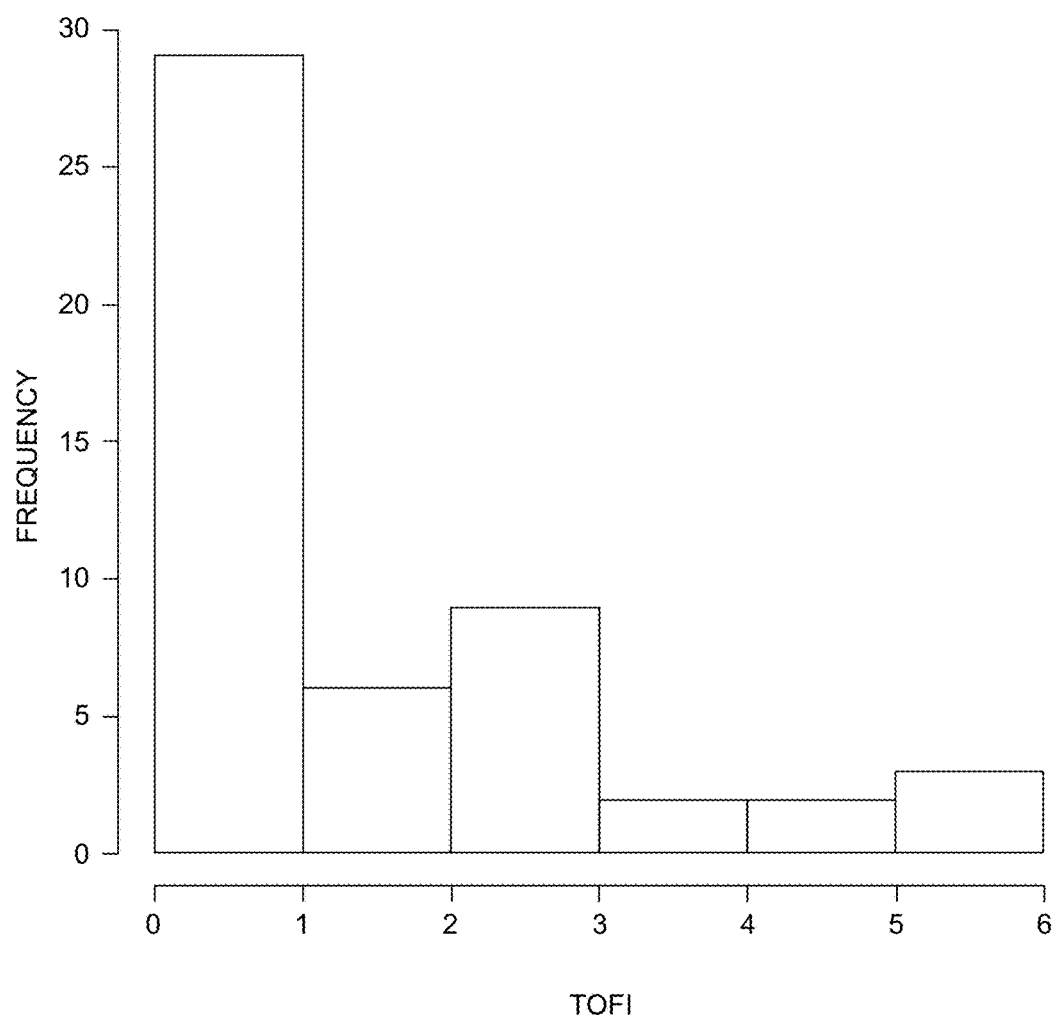
FIG. 6 illustratively depicts a histogram of a distribution of TOFI score values for a cohort of ToF patients, where the TOFI score uses a Cox Proportional Hazards regression model.

FIG. 6 illustratively depicts a histogram of the distribution of TOFI score values for the Health Facts® cohort of ToF patients (N=51), where the TOFI score uses a Cox Proportional Hazards regression model. The distribution shows strong right-skewing, owing partly to the fact that ToF patients in the U.S. tend to receive surgical treatment relatively early (hence, the severity tends not to be permitted to progress greatly concomitant with long times awaiting surgery) and partly to the fact that severe right ventricular outflow tract obstruction (RVOTO) or other abnormalities that are correlated with elevated BNP and elevated relative BNP velocity are relatively uncommon.

Turning now to FIGS. 7A and 7B, example survival curves for TOFI score values are illustratively provided in FIG. 7B based on the representative values of the table shown in FIG. 7A, determined in accordance with an embodiment of the present invention. Here, the survival curve is determined as $S(t)=S_0(t)^{exp(TOFI-1.013)}$, where 1.013 is the population-mean TOFI score in the Health Facts® cohort, as determined using a Cox Proportional Hazards model; with the Y-axis representing computed survival probabilities and the X-axis is patient age in days.

Figure 8:
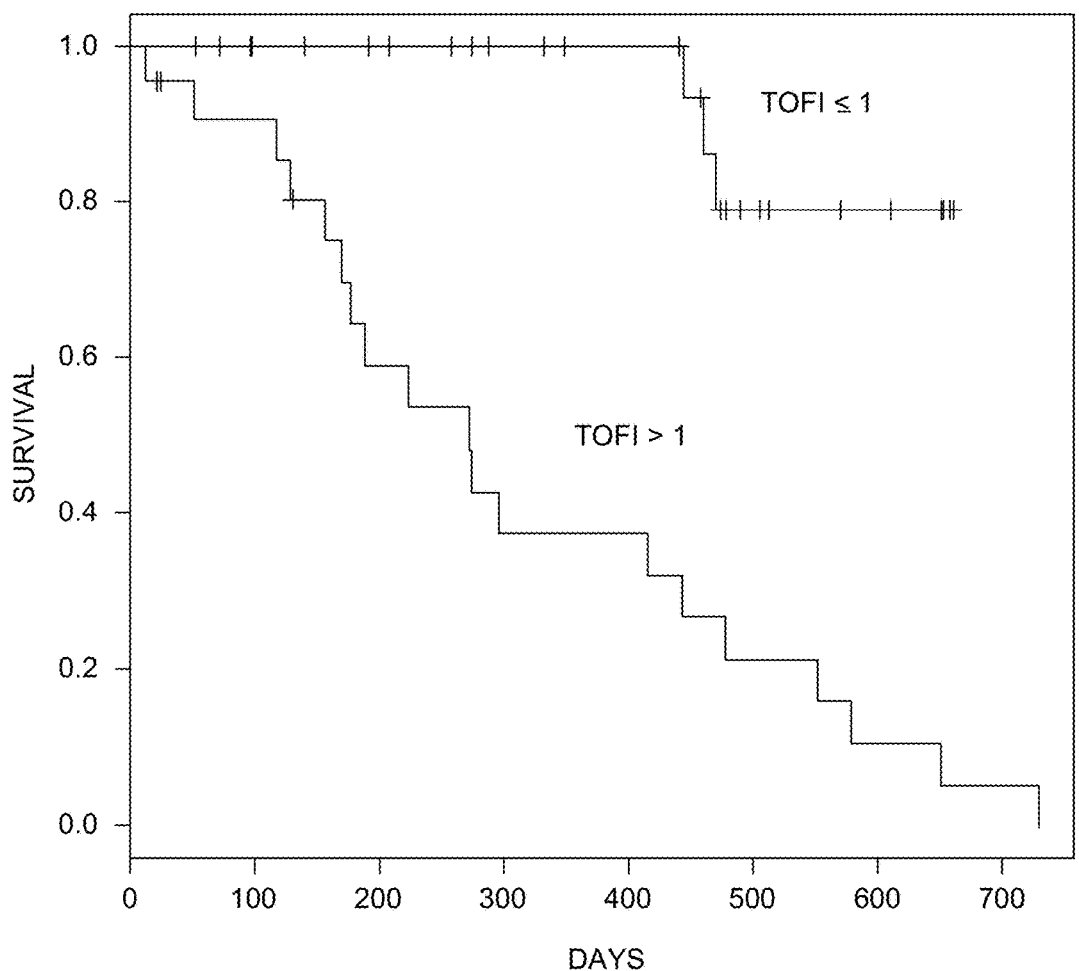
FIG. 8 illustratively depicts Kaplan-Meyer regressions of survival for the Health Facts® cohort of ToF patients and a classification of ToF severity according to decision-level categories or dichotomization cut-points or decision-points.

FIG. 8 illustratively depicts Kaplan-Meyer regressions of survival for the Health Facts® cohort of ToF patients and a classification of ToF severity according to decision-level categories or dichotomization cut-points or decision-points (such as TOFI>1), which yields significantly different prognosis for survival versus untreated patients. A product-moment regression such as the Kaplan-Meyer regressions shown here may be used for evaluating the predictive model and threshold decision-point. With reference to FIG. 8, the Y-axis is the survival rate and the X-axis represents time in days. Plus symbols represent members of the cohort who were censored, but were alive at that time; the Kaplan-Meyer product moment regression works to discount the influence of those censored data. From the data used here, 22 deaths occurred: 19 on the lower curve where TOFI>1 and 3 in the group where TOFI≤1.

Figure 9A:
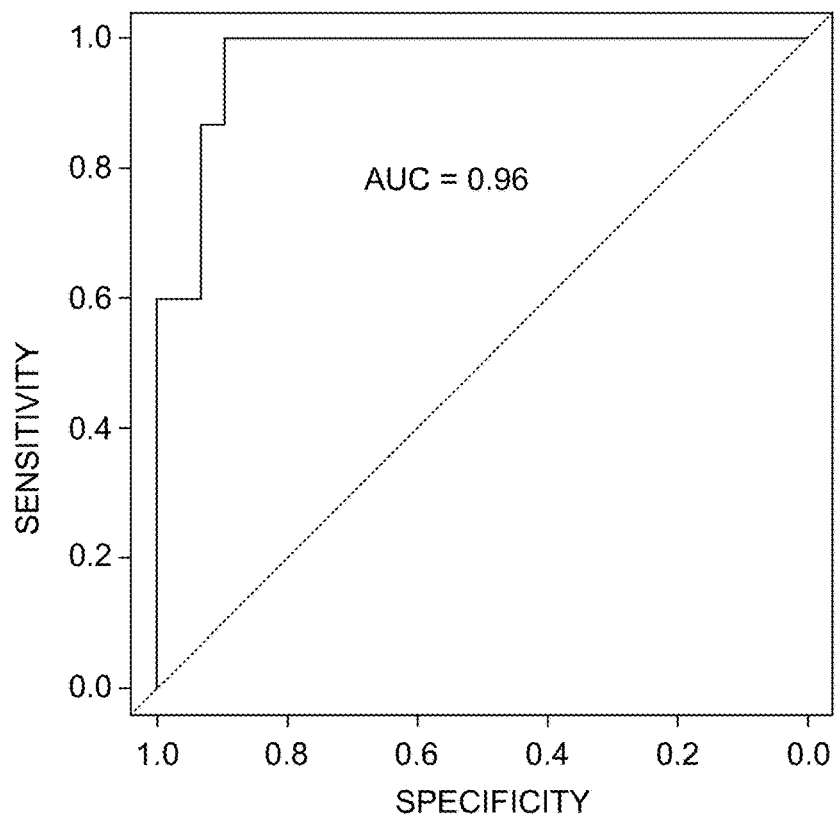
FIG. 9A illustratively depicts a ROC curve for establishing an optimal threshold value and evaluating the predictive model, and an associated contingency table, in accordance with an embodiment of the present invention.

Turning to FIGS. 9A-9D, with reference to FIG. 9A, the small Health Facts® cohort used for the example TOFI predictive model discussed in connection to FIGS. 4A-10B was associated with a high discrimination (ROC area under the curve=0.96), as shown in FIG. 9A, with the associated 2×7 contingency table. The left column of the table ("SURV2SURG") includes the number of patients who survived until surgery, corresponding to ranges of TOFI scores; the right column of the table ("DIED_A_SURG") indicates the number of patients who died before surgery. The total number of patients for each range of TOFI scores is shown to the right of the table.

In some embodiments, a TOFI score should be predictive of a specific outcome such as mortality, i.e. ideally the skilled person would like to be able to determine clinical outcome, for example survival or death, on the basis of such scores. A receiver operating characteristic (ROC) curve may allow this to be achieved. Such curves explore the relationship between the sensitivity and specificity of a clinical test, such as TOFI, for a variety of different cut points (or decision point), thus allowing the determination of an optimal cut point. For example, it will be desirable to set the threshold or select a decision point above which, deleterious outcome of the disease is indicated and below which survival is indicated.

Measures of performance of a clinical test can include sensitivity and specificity. Sensitivity is the probability that the disease (or outcome in some embodiments of the present invention) is diagnosed when it is actually present; and specificity is the probability that the disease is identified as being absent when it properly is absent. Ideally, both of sensitivity and specificity should be one. However, in some instances changing the cut point to try to increase one of sensitivity and specificity may result in a decrease in the other.

A ROC curve is a graphical technique for establishing an optimal cut point. In order to construct a ROC curve, the sensitivity and specificity are calculated for each possible cut point value. For the ROC graph, the X-axis is 1 minus the specificity and the Y-axis is the sensitivity. A diagonal line is drawn from the lower left corner to the upper right corner. This graph or curve reflects the characteristics of a test with no discriminating power. The closer the graph gets to the upper left corner the more effective it is at discriminating between cases and non-cases. Thus, an index of the goodness of the particular test is the area under the curve—the closer this value is to one, the better the discriminating power of the test. Accordingly, a ROC curve may be used to establish a cut point for a TOFI score, such that a score above the cut point may be indicative of deleterious outcome such as mortality, whereas a score below the cut point may be indicate of non-deleterious outcome such as survival.

In some embodiments, the decision point or cut point can be selected depending on the requirements of the test, for example whether it is more important to exclude false positives or whether it is more important to identify all true positives. For example, in the case of a test for identifying those patients admitted with severe ToF who are likely to die, it is important that all of the those patients are identified, even though this cut point may result identifying a number of false positives. In some embodiments, a cut point may indicate a particular outcome of ToF, such as survival, or be indicative of progression of ToF of increasing severity, or may indicate increased risk of other complications or comorbidities of ToF. As described above in connection to step 260 of method 200, in some embodiments, an appropriate cut point may be identified by a qualified clinician, caregiver. For example, a TOFI cut point of 1.0 can be a useful predictor when evaluating survival in patients suffering from ToF.

With reference to FIGS. 9B-9C, example data and calculations based on the data, are provided in a table herein referred to as 900. Table 900 includes columns 905-980 and a row for each of the 51 patients in the small Health Facts® cohort of ToF patients. Column 905 includes a number 1-51 corresponding to each of the 51 patients. Column 910 shows the last determined BNP amount for the patient, which could be determined such as described in connection to step 210 of method 200. Column 920 shows determined BNP velocities for each patient, which could be determined such as described in connection to steps 220 and 230 of method 200. Column 925 shows a determined relative or normalized velocity, which is determined in this embodiments as BNPV/BNP (or the value of column 920 divided by the value of column 910, for each patient). Column 930 shows the SDS1 variable, determined as max(0,(In(BNP)−4.3/0.56, wherein 4.3 is the mean and 0.56 is the standard deviation for BNP. Column 935 shows a variable SDS2' determined as max(0,(In(BNPV)−0.247/0.81 or logarithm of the absolute velocity. Column 940 shows a variable SDS2, determined as max(0,(In(VNORM)−2.8/0.64, where 2.8 and 0.64 are the mean and standard deviation, respectively, and VNORM is the relative velocity (column 925). Column 945 shows values for RL, a predictor variable shown in the algorithm presented in FIG. 9D. Column 950 shows the time (in days) corresponding to the recent BNP value of column 910. Column 960 shows the status of the patient and corresponds to the table of FIG. 9A, wherein a 0 indicates the patient survived until surgery and 1 indicates the patient did not. Column 970 shows the TOFI scores for each patient determined as $\beta 1$ SDS1+$\beta 2$ SDS2 (here, ROUND($\beta 1$*SDS1+($\beta 2$*SDS2,3)), where coefficients $\beta 1$ and $\beta 2$ are determined as 2.139 (rounded to 2.14) and 1.117 (rounded to 1.12). Column 980 indicates whether the TOFI score satisfies a threshold or cut point, set as 1 in this embodiment, such that a 1 indicates that the TOFI score is greater than 1 and 0 indicates that the score is less than 1. FIG. 9C also shows a table 901 of various statistical measures for the determined TOFI scores.

FIG. 9D shows an example algorithm for determining the TOFI score using Cox proportional hazards models for the 51 patients in the small Health Facts® cohort of ToF patients.

Figure 10B:
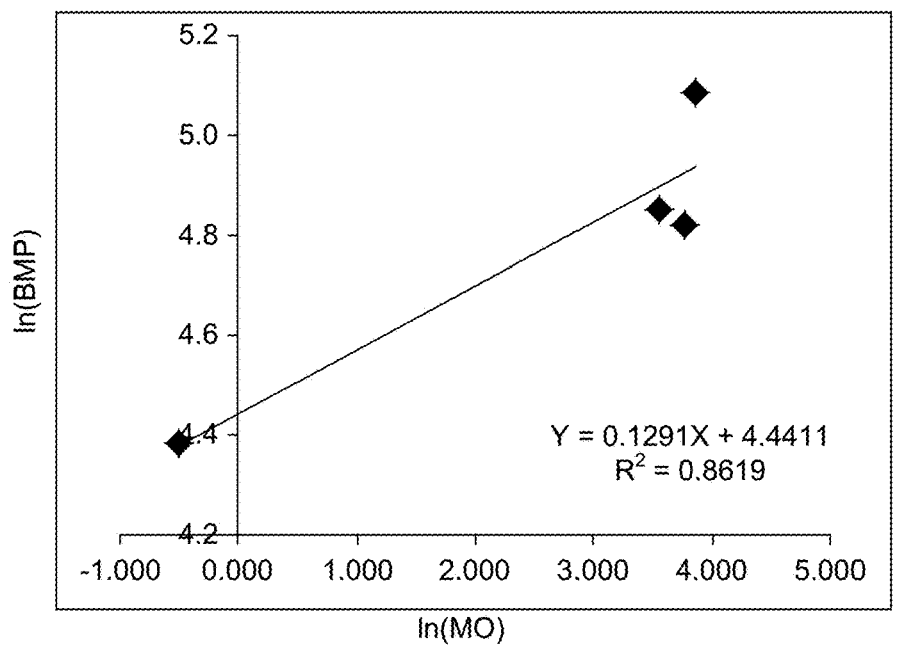
Figure 10B:
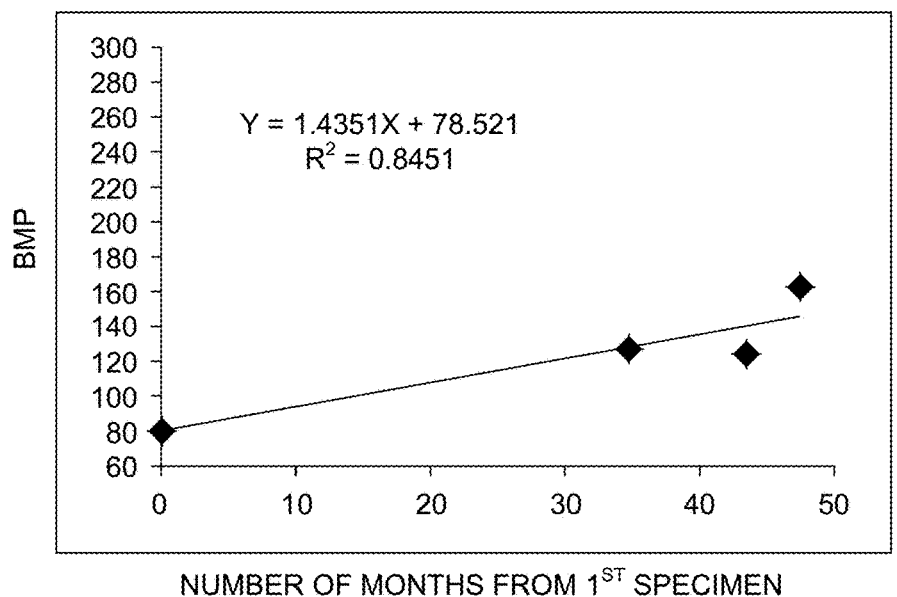

Turning now to FIGS. 10A and 10B, example embodiments of graphical user interfaces are provided for receiving patient information and displaying results, including diagnostic feedback, to a clinician or caregiver. In this example, first user interface component 1010 facilitates receiving patient data including biomarker information, wherein in this example, the biomarker information includes BNP values and corresponding times (dates) that the BNP values were determined. In this example, first user interface component 1010 indicates that four BNP values have been received, each corresponding to a different date. First user interface component 1010 can include fields for subsequent BNP values and corresponding dates (e.g., "BNP #5" and "Date of the fifth BNP"), which are unpopulated (unused) in this example. User interface component 1050 facilitates displaying results, including time between BNP measurements, BNP velocity and other information about the changing BNP levels, such as whether the rate has increased. In some embodiments, second user interface component 1050 includes feedback for a clinician or caregiver indicating possible errors in the provided data or whether all of the data needed for the calculations has been provided (e.g., "data complete?"). FIG. 10B depicts a table of calculated results based on the information provided in interface components 1010 and 1050, and graphs of the results shown in the table.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the invention. For example, although BNP-related biomarkers are primarily discussed in many of the embodiments presented herein, other biomarkers may be used indicative of change in the compensatory capacity of the heart muscle to deal with physiological loads placed upon it such as by ToF, ventricular septic defect, or other heart defects that cause the heart muscle to overwork.

It will be understood that certain features and subcombinations are of utility and may be employed without reference to other features and subcombinations and are contemplated within the scope of the claims. Not all steps listed in the various figures need be carried out in the specific order described.

The invention claimed is:

1. One or more computer-readable hardware media having computer-executable instructions embodied thereon that when executed, facilitate a method of clinical decision-making, the method comprising:
   receiving a first measurement of at least one of Brain Natriuretic Peptide (BNP), N-terminal Brain Natriuretic Peptide (NT-BNP), and pro-NT-BNP levels for a patient, the first measurement taken at a first time;
   receiving a second measurement of the at least one of BNP, NT-BNP, and pro-NT-BNP levels for the patient, the second measurement taken at a second time;
   receiving a set of information associated with a reference population of one or more patients having Tetralogy of Fallot;
   based on at least the first measurement taken at the first time and the second measurement taken at the second time, determining a rate of change for the at least one of BNP, NT-BNP, and pro-NT-BNP levels;
   determining a first z-score based on a timed measurement of the at least one of BNP, NT-BNP, and pro-NT-BNP levels and a second z-score based on the determined rate of change for the at least one of BNP, NT-BNP, and pro-NT-BNP levels;
   determining a severity score indicative of Tetralogy of Fallot for the patient by applying the first z-score and the second z-score to a predictive model;
   generating a schedule for treating the patient based on the severity score determined using the first z-score based on the timed measurement of the at least one of BNP, NT-BNP, and pro-NT-BNP levels and the second z-score based on the rate of change for the at least one BNP, NT-BNP, and pro-NT-BNP levels; and
   based on the generated schedule, facilitating treatment of the patient by allocating resources through an automatically generated electronic communication that indicates the patient is designated for prioritized medical treatment.

2. The computer-readable hardware media of claim 1, wherein the set of information includes rate of change information for the at least one of BNP, NT-BNP, and pro-NT-BNP levels from the reference population, and wherein determining a severity score further comprises comparing the rate of change information for the at least one of BNP, NT-BNP, and pro-NT-BNP levels from the reference population with the determined rate of change for the at least one of BNP, NT-BNP, and pro-NT-BNP levels associated with the patient.

3. The computer-readable hardware media of claim 1, further comprising wherein applying the predictive model comprises determining a probability of survival.

4. The computer-readable hardware media of claim 3, wherein determining a schedule for treating the patient comprises assigning a priority for treatment of the patient based on the determined probability of survival.

5. The computer-readable hardware media of claim 1, wherein the predictive model comprises a Cox proportional Hazards model.

6. The computer-readable hardware media of claim 1, wherein determining a schedule for treating the patient comprises assigning a priority for treatment of the patient based on the severity score.

7. The computer-readable hardware media of claim 1, wherein the determined severity score or the determined schedule for treating the patient is presented to a human decision-maker via an electronic medical record software system or device.

8. The computer-readable hardware media of claim 1, wherein the first time for taking the first measurement and the second time for taking the second measurement are at least sixty days apart.

9. The computer-readable hardware media of claim 1, wherein the timed measurement used for determining the first z-score is the second measurement of the at least one BNP, NT-BNP, and pro-NT-BNP levels.

10. A computer-implemented method to prioritize medical treatment for Tetralogy of Fallot in a population of human infants, the method comprising generating a recommendation for modifying treatment for a set of members in the population who exhibit above-threshold values of a severity score indicative of Tetralogy of Fallot calculated, for each member in the population, at least in part from a first z-score determined from a first timed measurement of at least one of BNP, NT-BNP, and pro-NT-BNP levels and a second z-score determined from a rate of change of an amount of the at least one of BNP, NT-BNP, and pro-NT-BNP determined from at least a first biomarker measurement taken at a first time and a second biomarker measurement taken at a second time for a patient within the population.

11. The computer-implemented method according to claim 10, wherein the recommendation for modifying treatment comprises a recommendation for at least one of prioritizing surgical correction, transferring to a particular treatment facility, or ordering additional testing.

12. The computer-implemented method according to claim 10, wherein the threshold is determined based on survival rates of a reference population of human infants with Tetralogy of Fallot.

13. The computer-implemented method according to claim 12, wherein the threshold is further determined based on available resources for medical treatment.

14. The computer-implemented method according to claim 10, wherein the recommendation is presented to a human decision-maker via an electronic medical record software system or device.

15. The computer-implemented method according to claim 10, wherein the severity score is calculated based on applying the first z-score and the second z-score to a survival prediction model.

16. The computer-implemented method according to claim 15, wherein the survival prediction model is used to forecast mortality of members of the population of human infants.

17. One or more computer-readable hardware media having computer-executable instructions embodied thereon that when executed, facilitate a method of clinical decision-making, the method comprising:
receiving a first measurement of a biomarker for a patient with a pediatric cardiac condition, the first measurement taken at a first time;
receiving a second measurement of the biomarker for the patient, the second measurement taken at a second time;
receiving a set of information associated with a reference population of one or more patients having the pediatric cardiac condition;
determining a first z-score based on at least one timed measurement of the biomarker of the patient;
based on at least the first measurement taken at the first time and the second measurement taken at the second time, determining a rate of change for the biomarker;
determining a second z-score based on the rate of change for the biomarker;
determining a severity score indicative of the pediatric cardiac condition for the patient based on at least the determined rate of change and the set of information, wherein the first z-score and the second z-score are applied to a predictive model to determine the severity score;
generating a schedule for treating the patient based on the severity score determined using at least the determined rate of change and the second set of information; and
based on the generated schedule, facilitating treatment of the patient by allocating resources through an automatically generated electronic communication that indicates the patient is designated for prioritized medical treatment.

18. The computer-readable hardware media of claim 17, wherein determining the severity score is based, in part, on a mean severity score for the reference population determined from the set of information.

19. The computer-readable hardware media of claim 17, wherein the biomarker comprises Brain Natriuretic Peptide (BNP), N-terminal Brain Natriuretic Peptide (NT-BNP), or pro-NT-BNP.

20. The computer-readable hardware media of claim 17, wherein generating a schedule for treating the patient comprises assigning a priority for treatment of the patient.

* * * * *

UNITED STATES PATENT AND TRADEMARK OFFICE
CERTIFICATE OF CORRECTION

PATENT NO. : 10,468,137 B1
APPLICATION NO. : 14/304165
DATED : November 5, 2019
INVENTOR(S) : Douglas S. McNair et al.

Page 1 of 1

It is certified that error appears in the above-identified patent and that said Letters Patent is hereby corrected as shown below:

In the Drawings

FIG. 10A., reference numeral 1050, Line 09: Please remove "specimines" and replace with --specimens--.

FIG. 10A., reference numeral 1050, Line 09: Please remove "specimines" and replace with --specimens--.

In the Specification

Column 10, Line 10: Please remove "SHRs" and replace with --EHRs--.

Column 10, Line 12: Please remove "SHRs" and replace with --EHRs--.

Column 10, Line 14: Please remove "SHRs" and replace with --EHRs--.

Column 20, Line 49: Please remove "distributed adaptive knowledge operating system" and replace with --Distributed Adaptive Agent Knowledge Operating System--.

Column 23, Line 24: Please remove "(β2" and replace with --β2--.

Signed and Sealed this
Seventeenth Day of December, 2019

Andrei Iancu
*Director of the United States Patent and Trademark Office*